(12) United States Patent
Hegmann et al.

(10) Patent No.: US 8,383,085 B2
(45) Date of Patent: Feb. 26, 2013

(54) METHODS OF MAKING IRON-CONTAINING NANOPARTICLES

(75) Inventors: Torsten Hegmann, Winnipeg (CA);
Vinith Yathindranath, Winnipeg (CA);
David F. Moore, Rockville, MD (US);
Johan van Lierop, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 219 days.

(21) Appl. No.: 12/660,230

(22) Filed: Feb. 22, 2010

(65) Prior Publication Data

US 2010/0303730 A1 Dec. 2, 2010

Related U.S. Application Data

(60) Provisional application No. 61/217,335, filed on May 29, 2009.

(51) Int. Cl.
*A61K 49/10* (2006.01)
*A61K 9/14* (2006.01)

(52) U.S. Cl. ........ 424/9.32; 424/632; 424/646; 424/489

(58) Field of Classification Search .................. 423/632, 423/633, 634; 428/403, 900; 424/9.32, 489, 424/632, 633, 634; 75/345, 351; 435/325, 435/235.1; 977/773, 906
See application file for complete search history.

(56) References Cited

U.S. PATENT DOCUMENTS

| | | | | |
|---|---|---|---|---|
| 6,962,685 | B2 * | 11/2005 | Sun ............................... | 423/632 |
| 8,167,972 | B2 * | 5/2012 | Ito et al. ........................... | 75/345 |
| 2003/0190475 | A1 * | 10/2003 | Carpenter et al. ............ | 428/403 |
| 2005/0191231 | A1 * | 9/2005 | Sun ............................... | 423/632 |
| 2007/0264199 | A1 * | 11/2007 | Labhasetwar et al. ....... | 424/9.32 |

OTHER PUBLICATIONS

Yuan-Pang Sun et al., A method for the preparation of stable dispersion of zero-valent iron nanoparticles, Colloids and Surfaces A: Physiochem, Eng. Aspects 308, 60-66, 2007.*
Anzai et al., "Iron oxide-enhanced MR lymphography: The evaluation of cervical lymph node metastases in head and neck cancer," *J. Magn. Reson. Imaging*, Jan.-Feb. 1997, 7(1), 75-81.
Anzai et al., "MR angiography with an ultrasmall superparamagnetic iron oxide blood pool agent," *J. Magn. Reson. Imaging*, Jan.-Feb. 1997, 7(1), 209-214.
Bilecka et al., "One-minute synthesis of crystalline binary and ternary metal oxide nanoparticles," *Chem. Commun.*, Feb. 21, 2008, 7, 886-888. Available online Dec. 19, 2007.
Bulte et al., "Magnetodendrimers allow endosomal magnetic labeling and in vivo tracking of stem cells," *Nat. Biotechnol.*, Dec. 2001, 19, 1141-1147.
Cheng et al., "Characterization of aqueous dispersions of $Fe_3O_4$ nanoparticles and their biomedical applications," *Biomaterials*, Mar. 2005, 26(7), 729-738.

Cushing et al., "Recent Advances in the Liquid-Phase Syntheses of Inorganic Nanoparticles," *Chem. Rev.*, 2004, 104(9), 3893-3946. Available online Aug. 20, 2004.
Du et al., "Preparation and characterization of Co-Pt bimetallic magnetic nanoparticles," *J. Magn. Magn. Mater.*, Apr. 2006, 299(1), 21-28. Available online Apr. 7, 2005.
Enochs et al., "Improved delineation of human brain tumors on MR images using a long-circulating, superparamagnetic iron oxide agent," *J. Magn. Reson. Imaging*, Feb. 1999, 9(2), 228-232.
Figuerola et al., "One-Pot Synthesis and Characterization of Size-Controlled Bimagnetic FePt-Iron Oxide Heterodimer Nanocrystals," *J. Am. Chem. Soc.*, 2008, 130(4), 1477-1487. Available online Jan. 9, 2008.
Ge et al., "Superparamagnetic Magnetite Colloidal Nanocrystal Clusters" *Angew. Chem., Int. Ed.*, 2007, 46(23), 4342-4345. Available online Apr. 30, 2007.
Gun'ko et al., "Magnetic nanoparticles and nanoparticle assemblies from metallorganic precursors," *J. Mater. Sci. Mater. Electron.*, Jun. 2001, 12(4-6), 299-302.
Gupta et al., "Synthesis and surface engineering of iron oxide nanoparticles for biomedical applications," *Biomaterials*, Jun. 2005, 26(18), 3995-4021. Available online Dec. 10, 2004.
Hargrove et al., "Mössbauer measurements of magnetite below the Verwey transition," *Solid State Commun.*, Mar. 1, 1970, 8(5), 303-308.
Hartman et al., "Detecting and Treating Cancer with Nanotechnology," *Mol. Diagn. Ther.*, 2008, 12(1), 1-14.
Hayashi et al., "Magnetic and rheological properties of monodisperse $Fe_3O_4$ nanoparticle/organic hybrid," *J. Magn. Magn. Mater.*, Mar. 2009, 321(5), 450-457. Available online Oct. 18, 2008.
Hegmann et al., "A Versatile One-Pot Synthesis of Magnetite Nanoparticles: A Greener Approach" abstract, Canadian Society for Chemistry (CSC), Ottawa, Ontario, Canada, 2009, retrieved on May 18, 2009 from the internet <http://abstracts.csc2009.ca/00000833.htm>; 1 pg.
Hoshino et al., "Physicochemical Properties and Cellular Toxicity of Nanocrystal Quantum Dots Depend on Their Surface Modification," *Nano Lett.*, 2004, 4(11), 2163-2169. Available online Oct. 16, 2004.
Huang et al., "Synthesis of Iron Nanoparticles via Chemical Reduction with Palladium Ion Seeds," *Langmuir*, 2007, 23(3), 1419-1426. Available online Dec. 9, 2006.
Hyeon et al., "Synthesis of Highly Crystalline and Monodisperse Maghemite Nanocrystallites without a Size-Selection Process," *J. Am. Chem. Soc.*, 2001, 123(51), 12798-12801. Available online Nov. 29, 2001.
Jander et al., "Imaging Inflammation in Acute Brain Ischemia," *Stroke*, 2007, 38, 642-645.
Kang et al., "Synthesis and Characterization of Nanometer-Size $Fe_3O_4$ and $\gamma$-$Fe_2O_3$ Particles," *Chem. Mater.*, 1996, 8(9), 2209-2211. Available online Sep. 12, 1996.
Kim et al., "Synthesis of ferrofluid with magnetic nanoparticles by sonochemical method for MRI contrast agent," *J. Magn. Magn. Mater.*, Mar. 2005, 289, 328-330. Available online Nov. 30, 2004.

(Continued)

*Primary Examiner* — Michael G Hartley
*Assistant Examiner* — Jagadishwar Samala
(74) *Attorney, Agent, or Firm* — Mueting Raasch & Gebhardt, P.A.

(57) ABSTRACT

A method of making iron-containing nanoparticles (e.g., magnetite nanoparticles) that includes contacting an iron-containing precursor with a reducing agent at a temperature less than 200° C. and allowing the mixture to react to form magnetite nanoparticles.

19 Claims, 16 Drawing Sheets

OTHER PUBLICATIONS

Kohler et al., "A Bifunctional Poly(ethylene glycol) Silane Immobilized on Metallic Oxide-Based Nanoparticles for Conjugation with Cell Targeting Agents," *J. Am. Chem. Soc.*, 2004, 126(23), 7206-7211. Available online May 22, 2004.

La Mer et al., "Theory, Production and Mechanism of Formation of Monodispersed Hydrosols," *J. Am. Chem. Soc.*, Nov. 17, 1950, 72(11), 4847-4854.

Laurent et al., "Magnetic Iron Oxide Nanoparticles: Synthesis, Stabilization, Vectorization, Physicochemical Characterizations, and Biological Applications," *Chem Rev.*, Jun. 2008, 108(6), 2064-2110. Available online Jun. 11, 2008.

Lee et al., "Artificially engineered magnetic nanoparticles for ultra-sensitive molecular imaging," *Nat. Med.*, Jan. 2007, 13(1), 95-99. Available online Dec. 24, 2006.

Li et al., "One-Pot Reaction to Synthesize Water-Soluble Magnetite Nanocrystals," *Chem. Mater.*, Apr. 20, 2004, 16(8), 1391-1393. Available online Mar. 20, 2004.

Li et al., "Preparation of Water-Soluble Magnetite Nanocrystals from Hydrated Ferric Salts in 2-Pyrrolidone: Mechanism Leading to $Fe_3O_4$," *Angew. Chem. Int. Ed.*, 2005, 44, 123-126.

Lian et al., "Synthesis of magnetite nanorods and porous hematite nanorods," *Solid State Commun.*, Feb. 2004, 129(8), 485-490. Available online Dec. 9, 2003.

Liu et al., "One-pot polyol synthesis of monosize PVP-coated sub-5 nm $Fe_3O_4$ nanoparticles for biomedical applications," *J. Magn. Magn. Mater.*, Mar. 2007, 310(2, Part 3), e815-e817. Available online Nov. 16, 2006.

Massart, "Preparation of aqueous magnetic liquids in alkaline and acidic media," *IEEE Trans. Magn.*, Mar. 1981, 17(2), 1247-1248.

Miyawaki et al., "In Vivo Magnetic Resonance Imaging of Single-Walled Carbon Nanohorns by Labeling with Magnetite Nanoparticles," *Adv. Mater.*, 2006, 18(8), 1010-1014. Available online Apr. 7, 2006.

Neuwelt et al., "Delivery of Virus-sized Iron Oxide Particles to Rodent CNS Neurons," *Neurosurgery*, Apr. 1994, 34(4), 777-784 (20 pgs. article text and 5 pgs. of accompanying figures; 25 pgs. total).

Niederberger, "Nonaqueous Sol-Gel Routes to Metal Oxide Nanoparticles," *Acc. Chem. Res.*, 2007, 40(9), 793-800. Available online Apr. 27, 2007.

Park et al., "Model of Formation of Monodispersed Colloids," *J. Phys. Chem. B*, 2001, 105(47), 11630-11635. Available online Aug. 14, 2001.

Pecharsky et al., *Fundamentals of Powder Diffraction and Structural Characterization of Materials*, Kluwer Academic Publishers, Boston, MA, 2003, cover page, copyright page, and table of contents only; 11 pgs.

Pinna et al., "Magnetite Nanocrystals: Nonaqueous Synthesis, Characterization, and Solubility," *Chem. Mater.*, 2005, 17(11), 3044-3049. Available online May 7, 2005.

Privman et al., "Mechanism of Formation of Monodispersed Colloids by Aggregation of Nanosize Precursors," *J. Colloid Interface Sci.*, May 1, 1999, 213(1), 36-45.

Senéterre et al., "Bone marrow: ultrasmall superparamagnetic iron oxide for MR imaging," *J. Radiology*, May 1991, 179(2), 529-533.

Shendruk et al., "The effect of surface spin disorder on the magnetism of $\alpha$-$Fe_2O_3$ nanoparticle dispersions," *Nanotech.*, 2007, 18, 455704(1-6). Available online Jun. 20, 2002.

Sun et al., "Size-Controlled Synthesis of Magnetite Nanoparticles," *J. Am. Chem. Soc.*, 2002, 124(28), 8204-8205. Available online Jun. 20, 2002.

Sun et al., "Monodisperse $MFe_2O_4$ (M = Fe, Co, Mn) Nanoparticles," *J. Am. Chem. Soc.*, 2004, 126(1), 273-279. Available online Dec. 10, 2003.

Sun, "Recent Advances in Chemical Synthesis, Self-Assembly, and Applications of FePt Nanoparticles," *Adv. Mater.*, 2006, 18, 393-403.

Veiseh et al., "Optical and MRI Multifunctional Nanoprobe for Targeting Gliomas," *Nano Lett.*, 2005, 5(6), 1003-1008. Available online Apr. 30, 2005.

Weinstein et al., "Superparamagnetic iron oxide nanoparticles: diagnostic magnetic resonance imaging and potential therapeutic applications in neurooncology and central nervous system inflammatory pathologies, a review," *J. Cerebr. Blood Flow Metab.*, Jan. 2010, 30(1), 15-35. Available online Sep. 16, 2009.

Xu et al., "Synthesis of Magnetic Microspheres with Immobilized Metal Ions for Enrichment and Direct Determination of Phosphopeptides by Matrix-Assisted Laser Desorption Ionization Mass Spectrometry," *Adv. Mater.* 2006, 18(24), 3289-3293. Available online Dec. 11, 2006.

Yathindranath et al., "Simultaneously magnetically directed drug convection and MR imaging," *Nanotechnology*, Oct. 7, 2009, 20(40), 405101 (1-12). Available online Sep. 8, 2009.

Yin et al., "The effects of particle size and surface coating on the cytotoxicity of nickel ferrite," *Biomaterials*, Oct. 2005, 26(29), 5818-5826. Available online Apr. 15, 2005.

Yonezawa et al., "Easy Preparation of Stable Iron Oxide Nanoparticles Using Gelatin as Stabilizing Molecules," *Jpn. J. Appl. Phys.*, 2008, 47(2), 1389-1392. Available online Feb. 15, 2008.

Zeng et al., "Syntheses, Properties, and Potential Applications of Multicomponent Magnetic Nanoparticles," *Adv. Funct. Mater.*, 2008, 18, 391-400.

Zhang et al., "Magnetically Recyclable Fe@Pt Core—Shell Nanoparticles and Their Use as Electrocatalysts for Ammonia Borane Oxidation: The Role of Crystallinity of the Core," *J. Am. Chem. Soc.*, 2009, 131(8), 2778-2779. Available online Feb. 10, 2009.

\* cited by examiner

METHODS OF MAKING IRON-CONTAINING NANOPARTICLES

CROSS-REFERENCES TO RELATED APPLICATIONS

This application claims the benefit of U.S. Provisional Application No. 61/217,335, filed May 29, 2009, herein incorporated by reference in its entirety.

BACKGROUND OF THE INVENTION

Iron-containing nanoparticles (e.g., iron oxide nanoparticles or "iron oxide NPs" or "IONPs") may be used in a wide variety of applications including, but not limited to, many different medical applications.

Some methods of making iron-containing nanoparticles may include drawbacks, such as the use of toxic components that may not be suitable for one or more medical applications, the use of high reaction temperatures that may limit the choice of nanoparticle capping agents, and/or other drawbacks. Some methods may also include fractionation processes to separate the nanoparticles according to particle size.

IONPs may be prepared by a variety of methods. There are various methods of making IONPs such as co-precipitation, nonaqueous and aqueous sol-gel (Bilecka et al., "One-minute synthesis of crystalline binary and ternary metal oxide nanoparticles," *Chem. Commun.*, 2008, 886), microemulsion, hydrothermal/solvothermal (Sun et al., "Monodisperse $MFe_2O_4$ (M=Fe, Co, Mn) Nanoparticles," *J. Am. Chem. Soc.*, 2004, 126, 273-279), and sonochemical processes (Kim et al., "Synthesis of ferrofluid with magnetic nanoparticles by sonochemical method for MRI contrast agent," *J. Magn. Magn. Mater.*, 2005, 289, 328), which have been used with acceptable results. Among the aqueous phase syntheses, Massart's method of co-precipitation has been used for its simplicity and the final product is often comprised of both magnetite ($Fe_3O_4$) and maghemite ($\gamma$-$Fe_2O_3$). (Massart, "Preparation of aqueous magnetic liquids in alkaline and acidic media," *IEEE Trans. Magn.*, 1981,)7, 1247-1248.) In short, ferric and ferrous salts in a 2 to 1 ratio dissolved in deionised (DI) and deoxygenated water are precipitated as IONPs, by carefully adjusting the pH of the reaction mixture to 11 or above using a base, usually aqueous ammonia ($NH_3.H_2O$) or sodium hydroxide (NaOH). (Kang et al., "Synthesis and Characterization of Nanometer-Size $Fe_3O_4$ and $\gamma$-$Fe_2O_3$ Particles," *Chem. Mater.*, 1996, 8, 2209-2211.) Massart's method is a mild way of preparing bare IONPs and IONPs with hydrophilic coatings by a one-pot synthesis. Parameters including temperature and the ratio of iron salts control the final product formation. The pH has to be carefully monitored at each step from synthesis to purification of the final product. However, the final nanoparticle product usually consists of two phases, magnetite ($Fe_3O_4$) and maghemite ($\gamma$-$Fe_2O_3$). The draw-back with this aqueous phase synthesis is that variations in the molar ratio of the iron salts often result in complex changes to the crystal structure of the final IONPs and the final product is often a mixture of magnetite and maghemite (Massart, "Preparation of aqueous magnetic liquids in alkaline and acidic media," *IEEE Trans. Magn.*, 1981, 17, 1247-1248.). Also the procedure has difficulties in achieving IONPs with narrow size distributions.

To overcome these setbacks, a number of high-temperature syntheses were developed that follow a thermal decomposition of iron species such as iron(III)acetylacetonate, Fe $(acac)_3$, and iron pentacarbonyl, $Fe(CO)_5$, in an organic phase (or solvent). (Hyeon et al., "Synthesis of Highly Crystalline and Monodisperse Maghemite Nanocrystallites without a Size-Selection Process," *J. Am. Chem. Soc.*, 2001, 123, 12798-12801.)

Sun et al. reported an organic phase synthesis of monodisperse magnetite nanoparticles starting from $Fe(acac)_3$. (Sun et al., "Size-Controlled Synthesis of Magnetite Nanoparticles," *J. Am. Chem. Soc.*, 2002, 124, 8204-8205.) The precursor $Fe(acac)_3$ in phenyl ether, in the presence of 1,2-hexanediol, oleic acid, and oleyl amine was refluxed at 265° C. to yield magnetite nanoparticles that are 4 nm in diameter. (Sun et al., "Size-Controlled Synthesis of Magnetite Nanoparticles," *J. Am. Chem. Soc.*, 2002, 124, 8204-8205.) Larger IONPs of 8, 12 and 16 nm were synthesized starting from these 4 nm particles in the presence of varying concentration of the precursor $Fe(acac)_3$, via a seed-mediated growth procedure. (Sun et al., "Size-Controlled Synthesis of Magnetite Nanoparticles," *J. Am. Chem. Soc.*, 2002, 124, 8204-8205.)

Pinna et al. disclosed a high-temperature synthesis of magnetite nanoparticles from $Fe(acac)_3$ in the absence of a specific surfactant molecules, where benzyl alcohol serves both as solvent and protective ligand. (Pinna et al., "Magnetite Nanocrystals: Nonaqueous Synthesis, Characterization, and Solubility," *Chem. Mater.*, 2005, 17, 3044-3049.) The precursor is thermally decomposed at 200° C. to yield magnetite particles with an average diameter of 20 to 25 nm. (Pinna et al., "Magnetite Nanocrystals: Nonaqueous Synthesis, Characterization, and Solubility," *Chem. Mater.*, 2005, 17, 3044-3049.)

Other strategies may include a sol-gel process that may require high temperatures and bulky hydrophobic organic surfactant molecules to yield monodisperse IONPs. In a sol-gel method using high temperatures, 15-nm $Fe_3O_4$ particles were made from a metal alkoxide ($Fe(O-tBu)_2(THF)_2$) at 300° C. (Gun'ko et al., "Magnetic nanoparticles and nanoparticle assemblies from metallorganic precursors," *J. Mater. Sci. Mater. Electron.*, 2001, 12(4-6), 299-302.) Others have reported yielding reasonably monodisperse IONPs, while following such high-temperature protocols. (Liu et al., "One-pot polyol synthesis of monosize PVP-coated sub-5 nm $Fe_3O_4$ nanoparticles for biomedical applications," *J. Magn. Magn. Mater.*, 2007, 310, e815-e817; Ge et al., "Superparamagnetic Magnetite Colloidal Nanocrystal Clusters" *Angew. Chem., Int. Ed.*, 2007, 46, 4342-4345; Figuerola et al., "One-Pot Synthesis and Characterization of Size-Controlled Bimagnetic FePt-Iron Oxide Heterodimer Nanocrystals," *J. Am. Chem. Soc.*, 2008, 130, 1477-1487; Xu et al., "Synthesis of Magnetic Microspheres with Immobilized Metal Ions for Enrichment and Direct Determination of Phosphopeptides by Matrix-Assisted Laser Desorption Ionization Mass Spectrometry," *Adv. Mater.* 2006, 18, 3289-3293.) The as-synthesized IONPs in high temperature organic-phase syntheses do not form colloidal solutions in aqueous and physiological media, which may render them unsuitable for many biomedical applications as such, and requires sophisticated post-preparative procedures to make them "water soluble." (Yin et al., "The effects of particle size and surface coating on the cytotoxicity of nickel ferrite," *Biomaterials,* 2005, 26, 5818-5826; Hoshino et al., "Physicochemical Properties and Cellular Toxicity of Nanocrystal Quantum Dots Depend on Their Surface Modification," *Nano Lett.*, 2004, 4, 2163-2169.) As a direct method, Gao et al. reported the high-temperature synthesis of 5-nm IONPs that are water soluble from $Fe(acac)_3$ and $FeCl_3.6H_2O$ by refluxing the precursors in 2-pyrrolidone which serves as solvent and ligand. (Li et al., "One-Pot Reaction to Synthesize Water-Soluble Magnetite Nanocrystals," *Chem. Mater.*, 2004, 16, 1391-1393; Li et al., "Preparation of Water-Soluble Magnetite Nanocrystals from Hydrated Ferric Salts in 2-Pyrrolidone: Mechanism Leading to $Fe_3O_4$,"*Angew. Chem. Int. Ed.*, 2005, 44, 123-126.)

Inorganic NP syntheses by precipitation may involve more simple steps and may need not require high temperatures. NPs may be precipitated out starting with soluble metal cations using reducing agents (e.g., gaseous $H_2$, solvated $NaBH_4$, hydrazine hydrate ($N_2H_4 \cdot H_2O$), or hydrazine dihydrochloride, etc.). Reduction of inorganic and organometallic precursors by sodium borohydride in metal NP synthesis has been used for gold, silver, iron (Huang et al., "Synthesis of Iron Nanoparticles via Chemical Reduction with Palladium Ion Seeds," *Langmuir*, 2007, 23, 1419-1426), cobalt (Du et al., "Preparation and characterization of Co—Pt bimetallic magnetic nanoparticles," *J. Magn. Magn. Mater.*, 2006, 299, 21-28), and other multi-component NPs. (Zeng et al., "Syntheses, Properties, and Potential Applications of Multicomponent Magnetic Nanoparticles," *Adv. Funct. Mater.*, 2008, 18, 391-400; Zhang et al., "Magnetically Recyclable Fe@Pt Core—Shell Nanoparticles and Their Use as Electrocatalysts for Ammonia Borane Oxidation: The Role of Crystallinity of the Core," *J. Am. Chem. Soc.*, 2009, 131, 2778-2779.) There have been reports on the synthesis of IONPs using sodium borohydride as a reducing agent. For example, Kinoshita et al. described the reduction and hydrolysis of aqueous $FeCl_3 \cdot 6H_2O$ in the presence of gelatine using aqueous sodium borohydride in an undisclosed ratio of components. (Yonezawa et al., "Easy Preparation of Stable Iron Oxide Nanoparticles Using Gelatin as Stabilizing Molecules," *Jpn. J. Appl. Phys.*, 2008, 47, 1389-1392.) These reaction conditions yielded maghemite ($\gamma$-$Fe_2O_3$) NPs with apparently no effective reduction of $Fe^{3+}$ to $Fe^{2+}$ observed.

Improved methods of making iron-containing nanoparticles, particularly surface-modified iron-containing nanoparticles, may be useful.

SUMMARY OF THE INVENTION

According to one aspect of the present disclosure, there is provided a method of making iron-containing nanoparticles (e.g., iron oxide nanoparticles or "IONPs"). The method includes contacting an iron-containing precursor with a reducing agent at a temperature less than 200° C. to form a mixture and allowing the mixture to react for a time sufficient to form magnetite nanoparticles, which may have an average size of at least 3 nanometers. In some embodiments, the mixture may further include a surfactant and/or a capping agent. In some embodiments, a surfactant or capping agent may be capable of providing a ligand to the iron-containing nanoparticles, thereby resulting in surface modification.

In one or more embodiments, the mixture may further include a deoxygenated mixture and the contacting may occur in a deoxygenated atmosphere (e.g., a nitrogen atmosphere).

According to another aspect of the present disclosure, there is provided a method of making selectively-sized iron-containing nanoparticles. The method includes providing a composition that includes an iron-containing precursor. The method also includes adding a reducing agent to the composition to form selectively-sized magnetite nanoparticles, wherein the molar ratio of the iron-containing precursor to the reducing agent is from 1:80 to less than 1:5 and wherein the reducing agent includes sodium borohydride. In some embodiments, the standard deviation of the size of the selectively sized magnetite nanoparticles may be less than 2 nanometers (nm).

According to another aspect of the present disclosure, there is provided a method of making magnetite nanoparticles. The method includes combining iron(III) acetylacetonate and deoxygenated ethanol with deoxygenated water to form a composition under a nitrogen atmosphere. The method includes adding sodium borohydride to the composition at a temperature from greater than 10° C. to 90° C. to form a mixture. The method includes allowing the mixture to react for a time sufficient to form magnetite nanoparticles.

Methods herein can include modifying the surface of the nanoparticles with, for example, surfactants and/or capping agents.

According to another aspect of the present disclosure, there is provided a use (e.g., a medical use) of the iron-containing nanoparticles made by the methods described herein. Such use may include, but is not limited to, use as a magnetic resonance imaging contrast agent, in a magnetically directed drug delivery, in a magnetic recording device, in a tumour treatment by hyperthermia, or magnetic tagging of a cell, a protein, a virus, and/or a gene.

The present disclosure may refer to IONPs by specifying, for example, the ligands (if any) attached thereto, the ratio of reducing agent to iron-containing precursor used to form the IONPs, and the temperature of the liquid in which the nanoparticles were formed. For instance, $IONP_{10(80)}$ refers to iron oxide nanoparticles that were formed in an 80° C. liquid with a 1:10 molar ratio of iron-containing precursor to reducing agent. In another example, $IONP\text{-}PEG_{40(RT)}$ refers to iron oxide nanoparticles that were formed in a room temperature ("RT") liquid with a 1:40 molar ratio of iron-containing precursor to reducing agent and have poly(ethylene) glycol ("PEG") ligands attached thereto. The term "room temperature" is used to mean temperatures in the range of 20° C. to 25° C. In another example, $IONP_{10(80)} \rightarrow OA$ refers to $IONP_{10(89)}$ coated with oleic acid post-synthesis (i.e., after the $IONP_{10(80)}$ was synthesized). In other words, the arrow notation ($\rightarrow$) indicates that the ligand that follows the arrow was coated on the IONP post-synthesis.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably.

As used herein, the term "or" is generally employed in its sense including "and/or" unless the content clearly dictates otherwise.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the accompanying drawings, which illustrate an exemplary embodiment of the present disclosure.

DETAILED DESCRIPTION OF ILLUSTRATIVE EMBODIMENTS OF THE INVENTION

Figure 1:
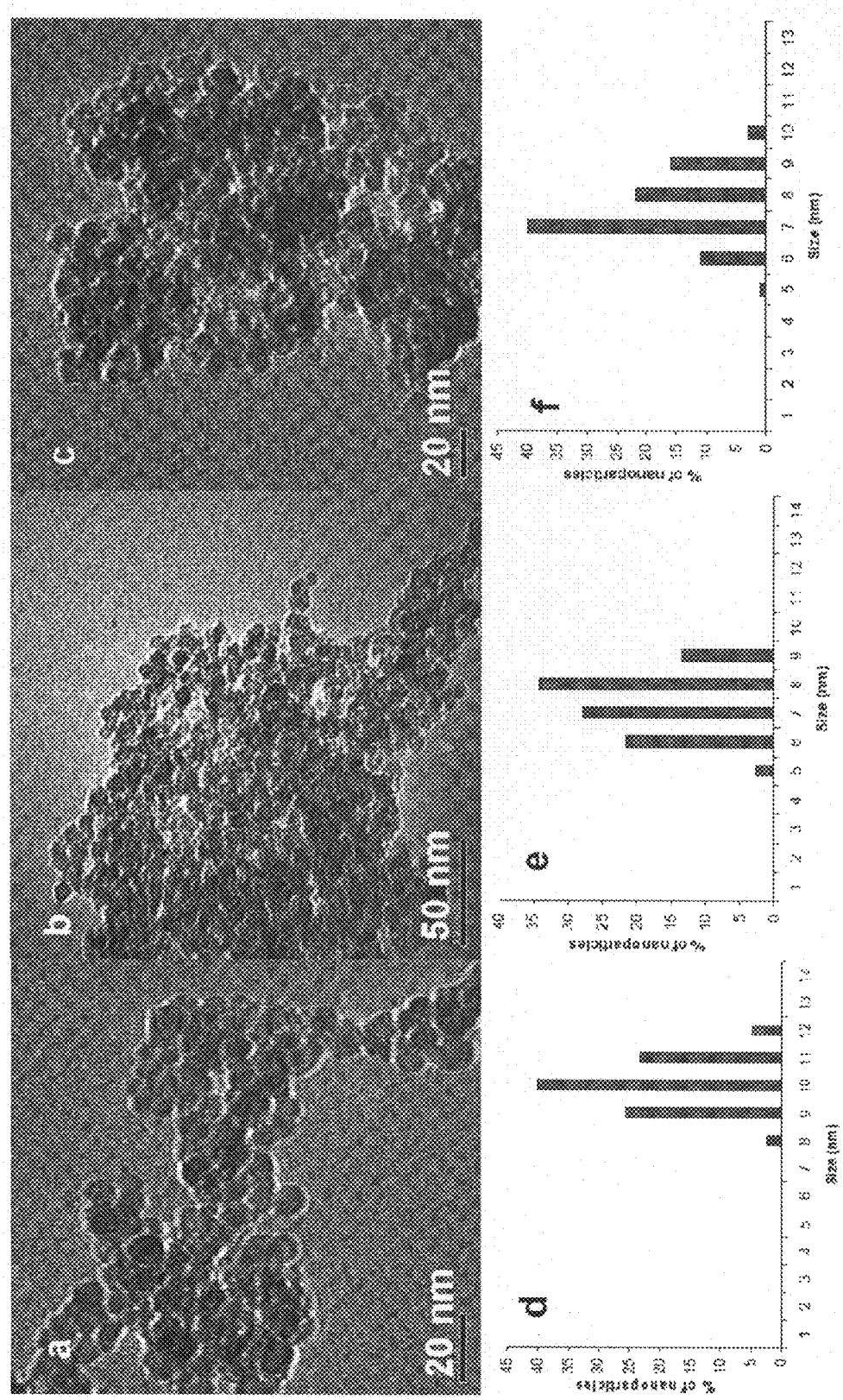
FIG. 1 shows transmission electron microscopy (TEM) micrograph images and size distribution histograms of: (a,d) bare magnetite NP [Fe(acac)$_3$: NaBH$_4$=1 mmol:10 mmol] IONP$_{10(80)}$; (b, e) bare magnetite NP [Fe(acac)$_3$:NaBH$_4$=1 mmol:40 mmol] IONP$_{40(80)}$; and (c, f) poly(ethylene) glycol-coated (PEG-coated) magnetite NP [Fe(acac)$_3$:NaBH$_4$=1 mmol:40 mmol] IONP-PEG$_{40(80)}$.

Surface modifications of IONPs with, for example, suitable polymers, drugs, and/or other functional moieties may be carried out post-synthesis, but may be accomplished in a more simple procedure, in-situ, during synthesis. One-pot synthesis of surface-modified IONPs according to one or more embodiments of the present disclosure refers to IONP surface modification (e.g., with ligands) wherein the surface modification occurs in-situ, during synthesis of the IONPs. One-pot synthesis of IONPs according to one or more embodiments of the present disclosure may include few non-toxic reagents and benign liquids (e.g., solvents), which may render such methods greener and sustainable methods of making IONPs that may be scaled up for bulk production.

According to one aspect of the present disclosure, there is provided a method of making iron-containing nanoparticles (e.g., iron oxide nanoparticles or "iron oxide NPs" or "IONPs"). The method may include contacting an iron-containing precursor with a reducing agent at a temperature less than 200° C. to form a mixture and allowing the mixture to react for a time sufficient to form magnetite nanoparticles. In some embodiments, the average size of the magnetite nanoparticles is at least 3 nanometers (nm). In some embodiments, the mixture may further include a surfactant and/or a capping agent. In one or more embodiments, the surfactant and/or capping agent may be capable of providing ligands to one or more iron-containing nanoparticles.

In one or more embodiments of the present disclosure, an iron-containing precursor may include an iron compound such as iron(III) acetylacetonate, which may be referred to herein as $Fe(acac)_3$. In some embodiments, the iron-containing precursor may include at least one bidentate ligand. In one or more embodiments of the present disclosure, an iron-containing precursor does not include $FeCl_3.6H_2O$. In some embodiments, an iron-containing precursor does not include iron chloride compounds. In some embodiments, an iron-containing precursor does not include halogenated iron compounds.

In one or more embodiments of the present disclosure, the mixtures of iron-containing precursor and reducing agent do not include gelatine.

In some embodiments, a reducing agent may be an inorganic reducing agent. A reducing agent may include one or more complex metal hydrides. In one or more embodiments, a reducing agent may include, but is not limited to, sodium borohydride ($NaBH_4$).

As used herein, a "coat" of ligands on a nanoparticle core means a nanoparticle core having a partial or, preferably, a complete monolayer of one specified ligand or ligand group.

Herein, a ligand is a molecule, ion, or atom that is attached to the central atom of a coordination compound, a chelate, or other complex. In some embodiments, a ligand may be a molecule, ion, or atom that is attached to a iron oxide NP (e.g., a magnetite nanoparticle).

In one or more embodiments of the present disclosure, a surfactant may include a hydrophilic surfactant and/or a hydrophobic surfactant. A wide variety of hydrophilic surfactants may be utilized in the methods of the present disclosure, including, but not limited to, poly(ethylene glycol) (PEG), glutamic acid (GA), L-arginine (LA), and R-arginine. A wide variety of hydrophobic surfactants may be utilized in the methods of the present disclosure, including, but not limited to, oleic acid (OA). In the present disclosure, any suitable surfactant may be used that is not reduced by the reducing agent under the conditions of nanoparticle formation and that may provide a ligand to iron-containing nanoparticles (e.g., magnetite nanoparticles). A suitable surfactant may include, for example, a hydrophilic portion (e.g., a polar functional group) and a hydrophobic portion (e.g., a lipophilic tail). A suitable surfactant may be capable of aggregating to make micelles or colloidal solutions.

In one or more embodiments, IONPs made by the methods described herein may or may not include surface modification. For example, IONPs may include hydrophilic ligands, may include hydrophobic ligands, or may be bare (i.e., have no ligands). IONPs having hydrophilic ligands may make such IONPs hydrophilic. IONPs having hydrophobic ligands may make such IONPs hydrophobic.

In one or more embodiments of the present disclosure, the mixture formed from the iron-containing precursor and reducing agent may also include a capping agent. In the present disclosure, a capping agent may be present during the formation of iron-containing nanoparticles and may be capable of providing ligands to the iron-containing nanoparticles (e.g., may be capable of forming a coating of ligands on the iron-containing nanoparticles). In some embodiments, a capping agent may coat a nanoparticle core (e.g., a magnetite nanoparticle core) with ligands. In some embodiments, a capping agent may include polymers and low molecular mass molecules that are compatible to the reaction conditions can be used to coat the IONPs in-situ.

In the present disclosure, any suitable capping agent may be used that is not reduced by the reducing agent under the conditions of nanoparticle formation and that may provide a ligand to the iron-containing nanoparticles (e.g., magnetite nanoparticles). In some embodiments, the capping agent may limit the nanoparticle growth during nanoparticle formation. In one or more embodiments, a capping agent may be capable of, for example, reducing aggregation and/or agglomeration of nanoparticles. In some embodiments, a capping agent may facilitate dispersion of the nanoparticles in a composition or mixture. Suitable capping agents include, but are not limited to, oleic acid, L-glutamic acid, R-glutamic acid, poly(ethylene glycol), L-arginine, and R-arginine.

In one or more embodiments, a surfactant may also be a capping agent (i.e., the surfactant and capping agent may be the same material). For example, materials that may be both a surfactant and a capping agent may include, but are not limited to, oleic acid, L-glutamic acid, R-glutamic acid, L-arginine, and R-arginine. In some embodiments, poly(ethylene) glycol is a capping agent, but not a surfactant. In some embodiments, the surfactant and capping agent may be different.

In one or more embodiments of the present disclosure, the iron-containing precursor may contact the reducing agent in a mixture, wherein the temperature of the mixture may be greater than 10° C., more preferably at least 20° C., even more preferably at least 25° C., even more preferably at least 50° C., or even more preferably at least 75° C. In some embodiments, the temperature of the mixture may be less than 200° C., more preferably no greater than 150° C., even more preferably no greater than 100° C., even more preferably no greater than 90° C., even more preferably no greater than 85° C., even more preferably no greater than 50° C., or even more preferably no greater than 30° C. In some embodiments, the temperature of the mixture may be from greater than 10° C. to less than 200° C. Preferably, the temperature may range from greater than 10° C. to 150° C., more preferably from greater than 10° C. to 100° C., even more preferably from greater than 10° C. to 90° C., even more preferably from greater than 10° C. to 85° C., even more preferably from greater than 10° C. to 50° C., even more preferably from greater than 10° C. to 30° C., and even more preferably from 20° C. to 30° C. In some embodiments, the temperature of the mixture may range from 75° C. to 85° C. In some embodiments, the temperature may be approximately 80° C.

In one or more embodiments, the mixture including the iron-containing precursor and reducing agent may further include a deoxygenated liquid. A liquid may be deoxygenated in a wide variety of methods (e.g., bubbling an inert gas through the liquid, consecutive freeze-pump-thaw cycles using an inert gas and/or vacuum) that are known to one of skill in the art. Preferably, a deoxygenated fluid does not include oxygen (e.g., dissolved oxygen). Herein, a deoxygenated liquid may include some oxygen (e.g., dissolved oxygen), such that the oxygen does not adversely affect magnetite nanoparticle formation in the liquid (e.g., reduce the yield of magnetite nanoparticles by forming, for example, maghemite nanoparticles in an amount of greater than 50 wt-% relative to the total weight of nanoparticles formed). Mixtures of deoxygenated liquids may also be used. Some suitable deoxygenated fluids for the present disclosure include water and alcohols (e.g., ethanol). In some embodiments, the contacting may occur in a deoxygenated atmosphere, such as an atmosphere of any inert gas (e.g., nitrogen, argon, etc.). Preferably, a deoxygenated atmosphere does not include any oxygen. However, a deoxygenated atmosphere may include some oxygen, such that the oxygen does not adversely affect magnetite nanoparticle formation in the liquid (e.g., reduce the yield of magnetite nanoparticles by forming, for example, maghemite nanoparticles in an amount of greater than 50 wt-% relative to the total weight of nanoparticles formed).

In one or more embodiments, the iron-containing precursor may include a ligand (e.g., acetylacetonate) that may contribute oxygen in the reaction forming magnetite nanoparticles.

In one or more embodiments, the iron-containing nanoparticles may include iron oxide nanoparticles (IONPs). In some embodiments, iron oxide nanoparticles may include magnetite nanoparticles. In one or more embodiments, the average size of the iron-containing nanoparticles (e.g., magnetite nanoparticles) may be at least 3 nanometers (nm), at least 4 nm, at least 5 nm, at least 6 nm, at least 7 nm, at least 8 nm, at least 10 nm, or at least 11 nm. In one or more embodiments, the average size of the iron-containing nanoparticles (e.g., magnetite nanoparticles) may be up to 12 nm, up to 11 nm, up to 10 nm, up to 9 nm, up to 8 nm, up to 7 nm, up to 6 nm, up to 5 nm, or up to 4 nm. In one or more embodiments, the average size of the iron-containing nanoparticles (e.g., magnetite nanoparticles) may be from 3 nanometers to 12 nanometers. In some embodiments, the average size of the iron-containing nanoparticles (e.g., magnetite nanoparticles) may be from 5 nm to 12 nm, may be from 5 nm to 10 nm, may be from 7 nm to 10 nm, may be from 7 nm to 8 nm, and/or may be from 8 nm to 10 nm. In some embodiments, the average size of the iron-containing nanoparticles (e.g., magnetite nanoparticles) may be from 10 nm to 12 nm and/or may be from 11 nm to 12 nm. In one or more embodiments, the average size of the iron-containing nanoparticles (e.g., magnetite nanoparticles) may be from 3 nm to 8 nm, from 4 nm to 7 nm, or from 5 nm to 6 nm.

The distribution of nanoparticle sizes may have a standard deviation of the nanoparticle sizes that may be less than 5 nm. More preferably, the standard deviation of the nanoparticle sizes may be less than 4 nm, even more preferably less than 3 nm, even more preferably less than 2 nm, even more preferably less than 1 nm.

Herein, the "size" of a particle is the largest dimension of the particle (e.g., the diameter if the particle is a sphere); the "average size" of a plurality of particles is the numerical average of the sizes, irrespective of distribution; and the "selected average size" of a plurality of particles is a desired particle size based on the selection of one or more particle formation parameters (e.g., ratio of reactants, temperature, etc.). Herein, a "size," as applied to a nanoparticle, is the largest dimension of the core of the nanoparticle, not the sum of the core and the ligands attached thereto.

In some embodiments of the present diclosure, the iron-containing nanoparticles formed by one or more of the methods of the present disclosure may include magnetite nanoparticles in an amount of 50 weight percent (wt-%) or more, relative to the total weight of nanoparticles formed. Iron-containing nanoparticles may include magnetite nanoparticles in an amount of (in increasing order of preference) 60 wt-% or more, 70 wt-% or more, 75 wt-% or more, 80 wt-% or more, 90 wt-% or more, 95 wt-% or more, 99 wt-% or more, or 99.9 wt-% or more, relative to the total weight of nanoparticles formed. In one or more embodiments, the iron-containing nanoparticles may all be magnetite nanoparticles.

The reducing agent may be provided in one or more embodiments as an aqueous mixture. In some embodiments, the amount of reducing agent (e.g., relative to the iron-containing precursor) to be contacted with the iron-containing precursor may be selectively chosen to make iron-containing nanoparticles of a selected size. In one or more embodiments, the temperature of iron-containing nanoparticle formation may be selectively chosen to make iron-containing nanoparticles of a selected size. In some embodiments, the temperature of iron-containing nanoparticle formation and the amount of reducing agent (e.g., relative to the iron-containing precursor) to be contacted with the iron-containing precursor may both be selectively chosen to make iron-containing nanoparticles of a selected size. A selected size of nanoparticles means a selected average size.

For example, in one or more embodiments when the temperature of iron-containing nanoparticle formation (i.e., the temperature of the surrounding liquid) is about 80° C., the molar ratio of the iron-containing precursor to the reducing agent may be selectively chosen (e.g., at 1:10) to obtain magnetite nanoparticles having a particular average size (e.g., about 8 nm). In one or more embodiment at 80° C., the molar ratio of the iron-containing precursor to the reducing agent may be selectively chosen (e.g., at 1:40, or a relative increase in reducing agent) to obtain magnetite nanoparticles having a smaller average size (e.g., about 5 nm). In one or more embodiments, when the molar ratio of the iron-containing precursor to the reducing agent is about 1:10, the temperature of iron-containing nanoparticle formation (i.e., the temperature of the surrounding liquid) may be selectively chosen at about 25° C. (or relatively lower) to obtain magnetite nanoparticles having a smaller average size (e.g., about 5 nm). In some embodiments, the molar ratio of reducing agent to iron-containing precursor and temperature may both be selectively chosen to obtain a desired magnetite nanoparticle size.

In one or more embodiments, contacting an iron-containing precursor with a reducing agent to form a mixture may include preparing a composition including water, an alcohol (e.g., ethanol), and the iron-containing precursor (and, optionally, e.g., a surfactant) at a temperature from greater than 10° C. to 85° C. and adding a reducing agent to the composition to form the mixture. In one or more embodiments, the mixture (e.g., of iron-containing precursors and reducing agent) may be heated and/or refluxed for any suitable amount of time to allow the mixture to react to form magnetite nanoparticles. In some embodiments, a suitable time may be 30 minutes or less. In some embodiments, a suitable time may be 20 minutes or less, 15 minutes or less, 10 minutes or less, or 5 minutes or less. In some embodiments, the time sufficient to form iron-containing nanoparticles may be more than 30 minutes.

In some embodiments of the present disclosure, the molar ratio of the iron-containing precursor to the reducing agent in the mixture may be less than 1:5 (i.e., one mole iron-containing precursor to greater than 5 moles reducing agent). In some embodiments, the molar ratio of the iron-containing precursor to the reducing agent in the mixture may be no greater than to 1:10, no greater than 1:20, no greater than 1:25, no greater than 1:40, no greater than 1:60, or no greater than 1:80. In some embodiments, the molar ratio of the iron-containing precursor to the reducing agent in the mixture may be at least 1:80, at least 1:60, at least 1:40, at least 1:25, or at least 1:10. In some embodiments, the molar ratio of the iron-containing precursor to the reducing agent in the mixture may be from 1:80 to less than 1:5. Preferably, the molar ratio of the reducing agent to the iron-containing precursor may be any ratio from 1:80 to 1:10, from 1:80 to 1:40, or from 1:40 to 1:10.

In one or more embodiments, a method of making iron-containing nanoparticles may further include collecting the iron-containing nanoparticles (e.g., magnetite nanoparticles) with a magnet (e.g., a rare earth magnet). A wide variety of magnetic materials known to one of skill in the art may be used. The method may also (or alternatively) include washing the iron-containing nanoparticles (e.g., magnetite nanoparticles). A wide variety of washing fluids may be used to wash the iron-containing nanoparticles including aqueous and/or non-aqueous fluids. In some embodiments, a washing fluid may include, but is not limited to, water, methanol, ethanol, hexane, etc. In some embodiments, the method may further include drying the iron-containing nanoparticles (e.g., magnetite nanoparticles). Drying the iron-containing nanoparticles may be accomplished under an inert gas (e.g., nitrogen, argon, etc.) using, for example, a stream (e.g., a constant stream) of inert gas. In one or more embodiments, drying may be accomplished using a desiccant, a mild heat below 100° C. (e.g., room temperature), and/or a mild vacuum.

In some embodiments, the method may further include adding iron-containing nanoparticles (e.g., magnetite nanoparticles) (e.g., in water) to a hydrophobic surfactant (e.g., oleic acid) and a non-aqueous fluid (e.g., an organic solvent, such as hexane, etc.). In some embodiments, agitating and/or sonicating the mixture may form magnetite nanoparticles that further include hydrophobic ligands. Iron-containing nanoparticles (e.g., magnetite nanoparticles) having hydrophobic ligands may be dispersed in a non-aqueous phase and may form a stable dispersion in a non-aqueous phase.

In one or more embodiments, the iron-containing nanoparticles (e.g., magnetite nanoparticles) may be formed in the absence or substantial absence of toxic organic surfactants. Herein, "toxic" organic surfactants means a surfactant that contributes a ligand to IONPs, wherein that coated IONP results in Caco2 and/or HepG2 cell viability of less than 75% after 24 hours when tested according to the cell viability procedure herein. Herein, "non-toxic" or "benign" organic surfactants means a surfactant that contributes a ligand to IONPs, wherein that coated IONP does not result in Caco2 and/or HepG2 cell viability of less than 75% after 24 hours when tested according to the cell viability procedure herein.

According to another aspect of the present disclosure, there is provided a method of making selectively-sized iron-containing nanoparticles (e.g., magnetite nanoparticles). The method may include providing a composition that includes an iron-containing precursor. The method may also include adding a reducing agent to the composition to form selectively-sized magnetite nanoparticles. In one or more embodiments, the molar ratio of the iron-containing precursor to the reducing agent may be from 1:80 to less than 1:5. The reducing agent may include sodium borohydride. In some embodiments of the present disclosure, the standard deviation of the size of the selectively sized magnetite nanoparticles may be less than 2 nanometers.

According to another aspect of the present disclosure, there is provided a method of making magnetite nanoparticles. The method may include combining iron(III) acetylacetonate and deoxygenated ethanol with deoxygenated water to form a composition under a nitrogen atmosphere. The method may include adding sodium borohydride to the composition at a temperature from greater than 10° C. to 90° C. (e.g., 25° C. or 80° C.) to form a mixture. The method may also include allowing the mixture to react for a time sufficient to form magnetite nanoparticles. In one or more embodiments, the composition may further include poly(ethylene glycol), oleic acid, L-glutamic acid, R-glutamic acid, L-arginine, and/or R-arginine.

According to another aspect of the present disclosure, the iron-containing nanoparticles (e.g., magnetite nanoparticles) in the present disclosure may be used in a wide variety of applications. These include, but are not limited to, use as a magnetic resonance imaging contrast agent, use in magnetically directed drug delivery; use in a magnetic recording device, use in tumour treatment by hyperthermia, or magnetic tagging of a cell, a virus, a protein, and/or a gene.

In one or more embodiments, magnetite nanoparticles prepared by one or more methods of the present disclosure may be used in medical applications, such as those disclosed and cited herein below. In one or more embodiments of the present disclosure, the magnetite nanoparticles formed may be ultrasmall superparamagnetic iron oxide nanoparticles (USPION) and may be useful in one or more applications using such nanoparticles. The synthesis of magnetic iron oxide nanoparticles (IONPs) with size control may be useful in preparing nanoparticles for such uses. IONPs having magnetite ($Fe_3O_4$) and/or maghemite ($\gamma$-$Fe_2O_3$) with a surface coating have been used in applications in, for example, clinical medicine as T2/T2* enhancing contrast agents for magnetic resonance imaging (MRI), as thermal mediators for tumour thermotherapy (e.g., by hyperthermia), and as vectors for targeted drug delivery and imaging. (Bulte et al., "Magnetodendrimers allow endosomal magnetic labeling and in vivo tracking of stem cells," Nat. Biotechnol., 2001, 19,1141-1147; Lee et al., "Artificially engineered magnetic nanoparticles for ultra-sensitive molecular imaging," Nat. Med., 2007, 13, 95-99; Miyawaki et al., "In Vivo Magnetic Resonance Imaging of Single-Walled Carbon Nanohorns by Labeling with Magnetite Nanoparticles," Adv. Mater., 2006, 18, 1010; Gupta et al., "Synthesis and surface engineering of iron oxide nanoparticles for biomedical applications," Biomaterials, 2005, 26, 3995-4021.) Coated IONPs have been considered for diagnostic and potential therapeutic applications involving central nervous system (CNS) disease conditions, such as blood-brain barrier (BBB) dysfunction in brain tumors, stroke, multiple sclerosis, epilepsy, and traumatic brain injury. (Weinstein et al., "Superparamagnetic iron oxide nanoparticles: diagnostic magnetic resonance imaging and potential therapeutic applications in neurooncology and central nervous system inflammatory pathologies, a review," J. Cerebr. Blood F. Met., 2010, 30, 15-35.) When administered intravenously, ultrasmall superparamagnetic iron oxide nanoparticles (USPION) can be detected in the CNS in neurons after BBB disruption, (Neuwelt et al., "Delivery of Virus-sized Iron Oxide Particles to Rodent CNS Neurons," Neurosurgery, 1994, 34, 777-784) as well as in malignant glial tumors (Enochs et al., "Improved delineation of human brain tumors on MR images using a long-circulating, superparamagnetic iron oxide agent," J. Magn. Reson. Imaging, 1999, 9, 228-232). Inside the human body, USPIONs may have a different organ distribution as compared to larger particles and may be useful for lymph node or bone marrow MRI. (Anzai et al., "Iron oxide-enhanced MR lymphography: The evaluation of cervical lymph node metastases in head and neck cancer," J. Magn. Reson. Imaging, 1997, 7, 75-81; Senéterre et al., "Bone marrow: ultrasmall superparamagnetic iron oxide for MR imaging.," J. Radiology, 1991, 179, 529-533.) With a longer blood half-life and T1-shortening effect, USPION can also be used as a blood-pool contrast agent for MR angiography (MRA). (Anzai et al., "MR angiography with an ultrasmall superparamagnetic iron oxide blood pool agent," J. Magn. Reson. Imaging, 1997, 7, 209-214.) IONPs with single domain may dissipate heat through domain dipole relaxation, termed as Neel relaxation, and the particles in the USPION range require far lower-strength magnetic fields to achieve the same effect as a larger ferromagnetic species for tumor thermotherapy. (Hartman et al., "Detecting and Treating Cancer with Nanotechnology," Mol. Diagn. Ther., 2008, 12, 1-14.) In addition, these particles may have the potential to be used for magnetically directed drug convection, to transport and enhance drug concentration at a particular site.

(Yathindranath et al., "Simultaneous magnetically directed drug convection and MR imaging," *Nanotechnology,* 2009, 20, 405101 (1-12).) Enhancing the effectiveness of the nanoparticles by manipulating the size and interfacial properties of the IONPs for specific biomedical applications though synthesis may be useful. (Kohler et al., "A Bifunctional Poly (ethylene glycol) Silane Immobilized on Metallic Oxide-Based Nanoparticles for Conjugation with Cell Targeting Agents,"*J. Am. Chem. Soc.,* 2004, 126, 7206-7211, Veiseh et al., "Optical and MRI Multifunctional Nanoprobe for Targeting Gliomas," *Nano Lett.,* 2005, 5, 1003-1008.) Better ways of making IONPs that are simple, easy to reproduce and biocompatible may be useful.

IONPs may be used in magnetic tagging of, for example, a cell (10-100 micrometers), a virus (20-450 nanometers), a protein (5-50 nanometers), and/or a gene (2 nanometers wide and 10-100 nanometers long). (Jander et al., "Imaging Inflammation in Acute Brain Ischemia," *Stroke,* 2007, 38, 642-645.) Iron oxide (magnetite and maghemite) is a ferrimagnetic mineral. The magnetic properties of iron oxide drastically varies depending on its size and temperature. (Sun, "Recent Advances in Chemical Synthesis, Self-Assembly, and Applications of FePt Nanoparticles," *Adv. Mater.,* 2006, 18, 393-403.) Superparamagnetic iron oxide nanoparticles (IONPs) may be useful as a T2 enhanced magnetic resonance imaging (MRI) contrast agent and drug carrier. Animal studies using surface-modified IONPs have established their ability to cross the blood-brain barrier (BBB) and deliver therapeutic agents inside the brain tissue. Strategies for synthesis of IONPs that are simple, economical, and free from unwanted toxic surfactant molecules may be useful.

The following examples are provided to illustrate one or more embodiments of the present disclosure. It will be understood, however, that the specific details given in each example have been selected for the purpose of illustration and are not to be construed as limiting in scope of the invention.

EXAMPLES

The examples include aqueous phase reduction/hydrolysis of $Fe(acac)_3$ using sodium borohydride at, for example, room temperature (RT). In comparison to other procedures, one or more of the examples did not include toxic organic solvents/surfactants, high temperatures, or a sophisticated apparatus to synthesize water dispersible IONPs. For example, IONPs were prepared at room temperature with a molar ratio of $NaBH_4$ to $Fe(acac)_3$ of 10:1. Also, for example, a series of $IONP_{X(80)}$ were synthesized with a reaction temperature of 80° C. and molar ratio of $NaBH_4/Fe(acac)_3$ of X=10, 25, 40, 60 and 80 (see Table 2). The methods presented in these examples were versatile for preparing bare and surface modified IONPs in-situ. To demonstrate this, hydrophilic PEG-coated (IONP-$PEG_{10(RT)}$, L-arginine-coated (IONP-$LA_{10(RT)}$), glutamic acid-coated (IONP-$GA_{10(RT)}$ and hydrophobic oleic acid-coated (IONP-$OA_{10(RT)}$) were prepared. Bare $IONP_{10(RT)}$ were also modified post-synthesis and such bare IONP were coated with hydrophobic OA by ultrasonication to yield $IONP_{10(RT)} \rightarrow OA$.

In these examples, an aqueous-phase synthesis (e.g., one-pot synthesis) of IONPs was conducted. This procedure was used to synthesize IONPs without a coating (i.e., bare IONPs), with a hydrophilic coating such as poly(ethylene glycol) (PEG), L-glutamic acid (GA), or L-arginine (LA), or with a hydrophobic coating such as oleic acid (OA).

Presented herein is the synthesis of magnetite NPs by reducing $Fe(acac)_3$ using sodium borohydride that was shown to be tolerant to the nature of the capping agent. The syntheses in these examples involved a liquid phase reduction of $Fe(acac)_3$ using sodium borohydride to yield IONPs of ranging sizes, with some size selection possible based on the reaction conditions. $Fe(acac)_3$ as a precursor was useful because of its low cost, stability, and ease of storage in comparison to some other iron salt precursors. Surface modification was carried out by using appropriate hydrophilic or hydrophobic surfactants such as poly(ethylene glycol) (PEG), L-glutamic acid (GA), oleic acid (OA), or L-arginine (LA) along with $Fe(acac)_3$ in a reaction vessel. Size selection was also achieved by, for example, varying the concentration of sodium borohydride with respect to $Fe(acac)_3$ and/or varying temperature. Thus, in some examples, size selection was achieved during the synthesis by varying the concentration of the reducing agent and/or by varying temperature. In this example, the reaction was complete in the relatively short time of about 30 minutes at, for example, a temperature of only 80° C. In comparison to other procedures, the reaction in one or more of these examples did not require bulky surfactant molecules to reduce and stabilize the final product, nor tedious size fractionation procedures. In short, reduced reaction time, low temperature, and a reduced number of reagents (e.g., that may be non-toxic) may provide an environmentally friendly (e.g., "greener"), more economical, and less expensive method of making IONPs. The environmentally benign reaction involving inexpensive reagents and a simple setup. (e.g., a reduced number of reagents) can easily be scaled up for large-scale, bulk production of IONPs.

Materials Used

All syntheses were carried out using reagents that are commercially available. Iron(III) acetylacetonate (99%) and polyethylene glycol 4000 (PEG) were purchased from Fluka (Sigma Aldrich (St. Louis, Mo.) is parent company), and were used without further purification. Oleic acid (OA), glutamic acid, sodium borohydride (freshly purchased) (98%) and 3-(4,5-dimethylthiazol-2-yl)-2,5-diphenyltetrazolium bromide were purchased from Sigma-Aldrich (St. Louis, Mo.). Millipore DI water (R=18 MΩ) was used throughout the experiments.

Testing Methods Used

Instrumentation. Powder x-ray diffraction (XRD) measurements were carried out on either a Siemens D5000 powder diffractometer equipped with a scintillation detector or on a Philips PW1710 powder x-ray diffraction system with a PW3830/40 x-ray generator. The data were processed using Jade data collection/processing software. Crystallite sizes were determined using a PANalytical X'Pert Pro Bragg-Brentano powder x-ray diffractometer equipped with a diffracted beam Ni-filter and an X'Celerator detector. Cu Kα radiation (λ=1.540598, 1.544426 E) were used as the x-ray source.

FT-IR for all the samples was recorded on Bruker TENSOR 27, using KBr pellets. KBr pellets were prepared by grinding 3 mg of IONPs in 150 mg anhydrous KBr and pressing using a hydraulic press.

Transmission electron microscopy (TEM) was carried out on a JEOL 2010F STEM. The NPs were diluted with methanol and a droplet was placed in a holey carbon film and was plasma cleaned prior to analysis. Transmission electron microscopy (TEM) was also carried out on a JEOL FEG-T/STEM. A 400 mesh copper grid with carbon support film was used to hold the NPs. The NPs were dispersed in either acetone or dichloromethane. A drop of the clear dispersed mixture was dropped onto the copper grid placed on a filter paper and allowed to dry under nitrogen.

Transmission Mφssbauer spectroscopy measurements were made at 10K with a Wissel spectrometer in constant acceleration mode calibrated using α-Fe at room temperature with a 1 GBq $^{57}$CoRh source. Spectra were collected in a Janis SHI-850 closed cycle refrigeration system.

Cell viability and morphology studies were conducted according to the following procedure. Caco2 and HepG2 cells were seeded in 96-well plates (5000 cells/well) and cultured in Dulbecco's Modified Eagle's Medium (DMEM) supplemented with 10% fetal bovine serum (FBS), 1% non-essential amino acids, 100 U/ml (enzyme activity Units per milliliter) benzylpenicilin, and 10 µg/ml streptomycin. Cells were maintained at 37° C. under a humidified atmosphere in a 5% $CO_2$ incubator. After one day in culture, cells were exposed to 200 µL of DMEM with varying concentrations of $IONP_{10(RT)}$ (0.01, 0.032, 0.1, 0.32 and 1 mg/ml) prepared according to the procedure in Example 1 below. After 24 hour exposure to $IONP_{10(RT)}$, the cells were then washed once and replenished with 200 microliters (µL) of fresh media and incubated for additional 48 hours (h). A total of 25 microliters (µL) of MTT reagent (5 mg/ml in phosphate buffered saline (PBS)) was added to each well and the cells were incubated for two hours in the 5% $CO_2$ incubator. After two hours, the purple formazan crystals were dissolved by adding a liquid (dimethylformamide(DMF):$H_2O$ in a volume ratio of 1:1) and incubated for 5 hours. The absorbance (A) was read at 570 nm using a plate reader (Synergy HT, by Biotek). The percentage cell viability of the wells treated with different concentrations of $IONP_{10(RT)}$ relative to control wells which received DMEM alone was calculated by $(A_{Sample}/A_{control}) \times 100$. For hematoxylin-eosin staining, Caco2 and HepG2 cells were seeded onto chamber slides and were treated with IONPs in a similar fashion to that of MTT assay. After 48 hours, the cells were washed and fixed.

Example 1

Synthesis of $IONP_{10(RT)}$ 0.7064 g (2 mmol) of $Fe(acac)_3$ was added to 100 ml of a 50/50 v/v water/ethanol mixture, which was then purged by bubbling nitrogen through the liquid for one hour. To this, at 25° C., 0.7566 g (20 mmol) of sodium borohydride was added with mechanical stirring under a nitrogen atmosphere. At this stage, evolution of $H_2$ gas was observed and the mixture turned from red to pale orange to black rapidly indicating the formation of nanoparticles. The reaction mixture was stirred at 1000 RPM for an additional hour. $IONP_{10(RT)}$ formed were magnetically separated using multiple cycles of washing with water, magnetically separating particles from water, washing with ethanol, and magnetically separating particles from ethanol. The particles were then dried under nitrogen at room temperature. The final product was a sooty-black powder.

Example 2

Synthesis of bare $IONP_{X(80)}$: (X=10, 25, 40, 60 and 80)

A mixture of 0.7064 g (2 mmol) of $Fe(acac)_3$ in 100 ml of 50/50 v/v water/ethanol mixture was purged with nitrogen for one hour. The reaction flask was placed in an oil bath and the temperature was raised to 80° C. with mechanical stirring (1000 RPM) under a steady nitrogen flow. Once the composition was at 80° C., required amounts of sodium borohydride were added according to the ratio of interest. The color of the reaction mixture in every case turned rapidly black and the contents were refluxed with continued stirring and under nitrogen atmosphere for an additional hour. The final IONP products were magnetically separated by using multiple cycles of washing with water, magnetically separating from water, washing with ethanol, and magnetically separating from ethanol. The IONPs were finally dried under nitrogen at room temperature.

Example 3

Synthesis of $IONP_{10(80)}$ and $IONP_{40(80)}$ 500 mg of $Fe(acac)_3$ in 100 ml of deoxygenated ethanol were added to 100 ml of deoxygenated water under nitrogen atmosphere in a round bottom flask. The composition was mechanically stirred at 1000 RPM for 15 minutes during which the temperature of the oil bath was gradually raised to 80° C. When a slight vapour started to evolve, 525 mg of aqueous sodium borohydride ($NaBH_4$) were added rapidly to the reaction flask. At this stage there was evolution of hydrogen gas and the colour of the reaction mixture turned from red to black rapidly (e.g., within about one minute). The reaction mixture was refluxed for an additional 30 minutes. The as-synthesized magnetite NPs $IONP_{10(80)}$ were collected using a rare earth magnet. The $IONP_{10(80)}$ were then repeatedly washed in and magnetically separated from water and washed in and magnetically separated from ethanol and dried under nitrogen at room temperature. The final product was a sooty-black powder.

For the synthesis of $IONP_{40(80)}$, the same procedure was used, except that a different amount of $NaBH_4$ (2.1 g of $NaBH_4$) was added rapidly to 500 mg of $Fe(acac)_3$ in the mixture. The final product was a sooty-black powder.

Example 4

Synthesis of $IONP\text{-}PEG_{10(RT)}$ 2.0 g (0.5 mmol) of PEG 4000 was added to 50 ml of DI water and the combination was purged with nitrogen. 0.7063 g (2 mmol) of $Fe(acac)_3$ was added to 50 ml of ethanol and was also purged (by bubbling) with nitrogen for one hour. The $Fe(acac)_3$ portion was mixed with the aqueous PEG portion to form a composition, and nitrogen was bubbled through the composition for additional 15 minutes along with stirring (1000 RPM). To this, at 25° C., 0.7566 g (20 mmol) of sodium borohydride was added and the reaction mixture rapidly turned from reddish to black color. The coated NPs were repeatedly washed by alternating between sonication in and magnetic separation from water, followed by sonication in and magnetic separation from ethanol, and then dried under nitrogen at room temperature.

Example 5

Synthesis of $IONP\text{-}PEG_{10(80)}$ 2 g of the PEG 4000 were dissolved in 100 ml of deoxygenated water. 500 mg of $Fe(acac)_3$ were dissolved in 100 ml of deoxygenated ethanol. The $Fe(acac)_3$ portion was added to the, aqueous PEG portion without exposing the portions to atmosphere and the temperature of the reaction flask was raised to 80° C. with stirring (1000 RPM). 525 mg of sodium borohydride were added rapidly. The reaction mixture rapidly turned from reddish to orange to black rapidly. The coated NPs were repeatedly washed using several cycles of sonication in and magnetic separation from water and then sonication in and magnetic separation from ethanol. The resulting black powder was dried under nitrogen to yield black coloured powder.

Example 6

Synthesis of IONP-PEG$_{40(80)}$

For the synthesis of IONP-PEG$_{40(80)}$, the procedure of Example 5 was used, except that a different amount of NaBH$_4$ (2.1 g of NaBH$_4$) was added rapidly to 500 mg of Fe(acac)$_3$ in the mixture. The final product was a black coloured powder.

Example 7

Synthesis of IONP-OA$_{10(RT)}$ 2 g (7 mmol) of OA was added to 50 ml of deoxygenated ethanol along with 0.7063 g (2 mmol) of Fe(acac)$_3$. To this, at 25° C., 0.7566 g (20 mmol) of sodium borohydride was added rapidly and the mixture was stirred at 1000 RPM for 15 minutes in a nitrogen atmosphere. Thereafter, 50 ml of DI and deoxygenated water was added and the mixture was stirred for one hour. The color of the final reaction was blackish green. The crude product was several times washed in and magnetically separated from ethanol, followed by washing in and magnetic separation from hexane to remove any free OA. The washed particles were then dried under a steady flow of nitrogen.

Example 8

Synthesis of IONP-OA$_{10(80)}$ 5 g of oleic acid was dissolved in 100 ml of deoxygenated ethanol along with 500 mg of Fe(acac)$_3$. The composition in ethanol was added to the reaction flask containing 100 ml of deoxygenated water without exposing to air. Slowly the temperature of the reaction flask was raised to 80° C. with stirring (1000 RPM). Once the composition reached the desired temperature (e.g., 80° C.), 525 mg of sodium borohydride dissolved in 10 ml of deoxygenated DI water was added rapidly inside the reaction flask and refluxed for 30 minutes. The final black precipitate obtained after several cycles of washing with ethanol, magnetically separating the particles from ethanol, washing in hexane (e.g., to remove any free oleic acid molecules), and magnetically separating the particles from hexane. The washed particles were then dried under a steady flow of nitrogen.

Example 9

Synthesis of IONP$_{10(80)}$→OA

As an alternative way, IONP$_{10(80)}$→OA was synthesized from IONP$_{10(80)}$ formed according to the procedure of Example 2. A dispersion of magnetite NPs (IONP$_{10(80)}$), 100 mg in 50 ml of DI water, was added to a mixture of 5 g of oleic acid in 50 ml hexane. At this stage, the magnetite particles were dispersed in the aqueous layer and would not pass into the hexane portion. The mixture in a round bottom flask was sonicated for 10 minutes at 25° C. with frequent (e.g., every few minutes) manual shaking. After 10 minutes, the NPs were completely transferred from the aqueous phase to the organic phase indicating the completion of oleic acid attachment to the surface of the NPs.

According to TEM, the particle size of IONP-OA$_{10(80)}$ was about 11 nanometers.

Example 10

Synthesis of IONP$_{10(RT)}$→OA

A dispersion of IONP$_{10(RT)}$ prepared by the procedure of Example 1 (100 mg in 50 ml of DI water) was added to a mixture of 5 grams (g) of OA in 50 ml hexane. Initially, IONP$_{10(RT)}$ were dispersed in the aqueous layer and would not transfer into the organic layer. The mixture in a round bottom flask was sonicated for one hour at 25° C. with occasional shaking. After 10 minutes, the NPs were completely transferred from the aqueous phase into the organic phase indicating the OA capping of the IONP surface.

Example 11

Synthesis of L-Glutamic Acid-Coated IONPs (IONP-GA$_{10(80)}$)

3.0 g (20 mmol) of L-glutamic acid (GA) was added to 50 ml of DI water (pH=3) and the pH was adjusted to 7.2 (using 1M sodium hydroxide solution), at which point the glutamic acid was completely dissolved and the solution was purged with nitrogen for one hour.

706.3 mg (2.0 mmol) of Fe(acac)$_3$ was dissolved in 50 ml of ethanol and nitrogen was bubbled through that fluid for one hour. The Fe(acac)$_3$ solution was combined with the aqueous amino acid portion and nitrogen was bubbled through that fluid for additional 15 minutes with stirring (1000 RPM). The reaction flask was placed in an oil bath and the temperature was raised to 80° C. with mechanical stirring (1000 RPM) under a steady nitrogen flow.

Once the composition was at 80° C., 756.6 mg (20 mmol) of sodium borohydride was added rapidly and the mixture turned from reddish to black color. The coated NPs were repeatedly washed by using several cycles of alternating between sonication and magnetic separation in water, followed by sonication and magnetic separation in ethanol. The nanoparticles were then dried under nitrogen at room temperature.

The size of the magnetite particles coated with glutamic acid was determined by XRD to be about 12 nm.

Example 12

Synthesis of L-Glutamic Acid-Coated IONPs (IONP-GA$_{10(RT)}$)

3.0 g (20 mmol) of glutamic acid (GA) was added to 50 ml of DI water (pH=3). The pH was adjusted to 7.2 (using 1M sodium hydroxide solution), at which point the glutamic acid was completely dissolved and the nitrogen gas was bubbled for one hour through the mixture.

706.3 mg (2.0 mmol) of Fe(acac)$_3$ was dissolved in 50 ml of ethanol and nitrogen was bubbled through that fluid for one hour. The Fe(acac)$_3$ solution was combined with the aqueous amino acid portion and nitrogen was bubbled through that composition for additional 15 minutes with stirring (1000 RPM).

To this, 756.6 mg (20 mmol) of sodium borohydride was added rapidly and the mixture turned from reddish to black color. The coated NPs were repeatedly washed by using several cycles of alternating between sonication and magnetic separation in water, followed by sonication and magnetic separation in ethanol. The nanoparticles were then dried under nitrogen at room temperature.

Example 13

Synthesis of L-Arginine-Coated IONPs (IONP-LA$_{10(RT)}$)

In case of L-arginine (LA), 3.5 g (20 mmol) of L-arginine was dissolved in 50 ml of DI water and nitrogen was bubbled through the fluid.

706.3 mg (2.0 mmol) of Fe(acac)$_3$ was dissolved in 50 ml of ethanol and nitrogen was bubbled through that fluid for one hour. The Fe(acac)$_3$ solution was combined with aqueous amino acid portion and nitrogen was bubbled through that composition for additional 15 minutes with stirring (1000 RPM).

To this, 756.6 mg (20 mmol) of sodium borohydride was added rapidly and the mixture turned from reddish to black color. The coated NPs were repeatedly washed by using several cycles of alternating between sonication and magnetic separation in water, followed by sonication and magnetic separation in ethanol. The nanoparticles were then dried under nitrogen at room temperature.

Detailed structural, compositional and size information for the synthesized IONPs was obtained using powder x-ray diffraction (XRD), transmission electron microscopy (TEM), selected area electron diffraction (SAED), Fourier transform infrared (FT-IR) spectroscopy and transmission Mössbauer spectroscopy.

TABLE 1

IONPs synthesized, and the ratio between precursor and reducing agent.

| NP | Capping agent | Ratio Fe(acac)$_3$:NaBH$_4$ |
| --- | --- | --- |
| IONP$_{10(RT)}$ | None | 1:10 |
| IONP$_{10(80)}$ | None | 1:10 |
| IONP$_{25(80)}$ | None | 1:25 |
| IONP$_{40(80)}$ | None | 1:40 |
| IONP$_{60(80)}$ | None | 1:60 |
| IONP$_{80(80)}$ | None | 1:80 |
| IONP-PEG$_{10(RT)}$ | PEG | 1:10 |
| IONP-PEG$_{10(80)}$ | PEG | 1:10 |
| IONP-PEG$_{40(80)}$ | PEG | 1:40 |
| IONP-OA$_{10(RT)}$ | OA | 1:10 |
| IONP-OA$_{10(80)}$ | OA | 1:10 |
| IONP$_{10(RT)}$→OA | OA | from IONP$_{10(RT)}$ |
| IONP$_{10(80)}$→OA | OA | from IONP$_{10(80)}$ |
| IONP-GA$_{10(80)}$ | GA | 1:10 |
| IONP-GA$_{10(RT)}$ | GA | 1:10 |
| IONP-LA$_{10(RT)}$ | GA | 1:10 |

The as-synthesized IONPs were characterized using powder x-ray diffraction (XRD), transmission electron microscopy (TEM), Fourier transform infra red (FT-IR) and Mössbauer spectroscopy. FIG. 1a shows the TEM images of the bare magnetite NPs (IONP$_{10(80)}$), obtained by reducing one millimole (mmol) of Fe(acac)$_3$ with 10 mmol of NaBH$_4$. The average particle size determined from one hundred particles is about 10 nanometers (nm) with a standard deviation of 0.8 nm. The IONP synthesized using 40 mmol of NaBH$_4$ to 1 mmol of Fe(acac)$_3$ (IONP$_{40(80)}$, FIG. 1b) had a smaller size at 7.4±1.0 nm. Similarly, the PEG-coated NPs synthesized with higher NaBH$_4$ concentration (IONP-PEG$_{40(80)}$, FIG. 1c) also showed a smaller size at 7.4±0.9 nm similar to IONP$_{40(80)}$. FIGS. 1d-f show the respective size distribution histograms of the NPs IONP$_{10(80)}$, IONP$_{40(80)}$, and IONP-PEG$_{40(80)}$.

Figure 5:
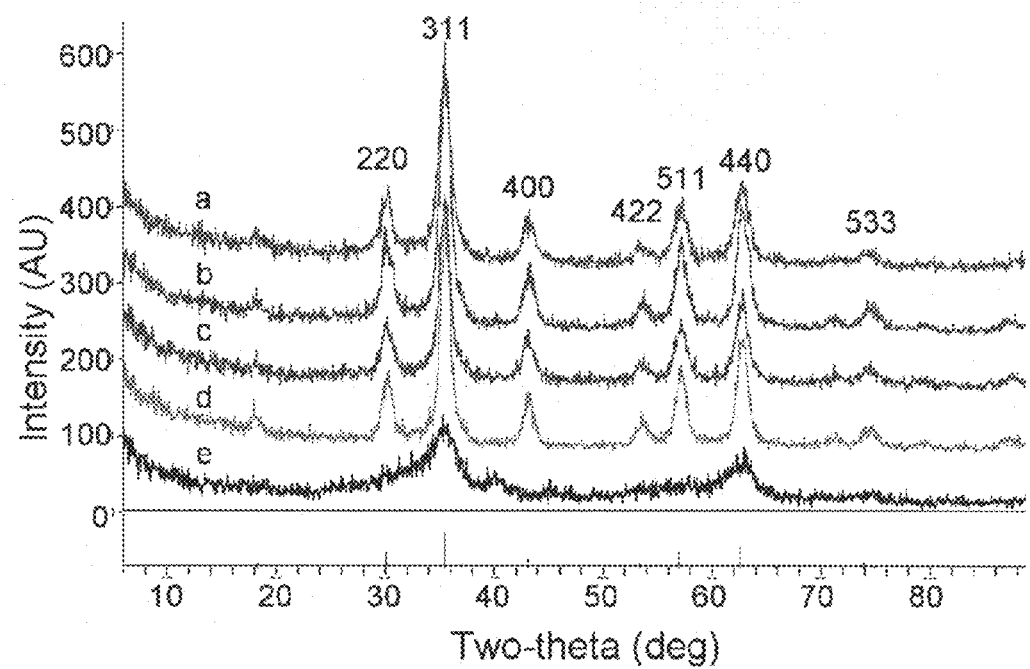
FIG. 5 shows the powder XRD (X-ray diffraction) pattern of (a) PEG-coated magnetite NP [Fe(acac)$_3$:NaBH$_4$=1 mmol:40 mmol] IONP-PEG$_{40(80)}$, (b) PEG-coated magnetite NPs IONP-PEG$_{10(80)}$ [Fe(acac)$_3$:NaBH$_4$=1 mmol:10 mmol], (c) bare magnetite NP [Fe(acac)$_3$:NaBH$_4$=1 mmol:40 mmol] IONP$_{40(80)}$, (d) bare magnetite NP [Fe(acac)$_3$:NaBH$_4$=1 mmol:10 mmol] IONP$_{10(80)}$, (e) bare magnetite NP [Fe(acac)$_3$:NaBH$_4$=1 mmol:5 mmol] IONP$_{5(80)}$. Literature values for the peak positions for bulk magnetite are shown as vertical lines below. The most prominent peaks are indexed.

FIG. 5 (line d) shows the powder XRD pattern of IONP$_{10(80)}$ synthesized with the Fe(acac)$_3$ and sodium borohydride concentration in the molar ratio of 1:10 and at a temperature of 80° C. From the diffraction pattern and peak positions, the NPs were identified as iron oxide with a cubic unit cell and were consistent with magnetite and maghemite. The diffraction peaks observed were broad as may be expected for smaller crystallite sizes. The average particle size calculated using Scherrer equation from the 311, 511 and 440 reflections was averaged to be 11.9 nm for IONP$_{10(80)}$. An increase in the concentration of NaBH$_4$ from 10 mmol to 40 mmol resulted in NPs with average crystallite size of 7 nm for IONP$_{40(80)}$ and IONP-PEG$_{40(80)}$. These values are in good agreement with the sizes obtained by analyzing the TEM images for these particles. The XRD pattern of IONP$_{40(80)}$ and IONP-PEG$_{40(80)}$ are shown in FIG. 5 (lines c and a, respectively). The XRD patterns for IONP$_{10(80)}$, IONP$_{40(80)}$, IONP-PEG$_{10(80)}$ and IONP-PEG$_{40(80)}$ are consistent with iron oxide (Fe$_3$O$_4$ and γ-Fe$_2$O$_3$); the standard peaks of which are shown at the bottom in FIG. 5. The IONP$_{5(80)}$ obtained with 5 equivalents of sodium borohydride had a less resolved magnetite phase.

Figure 4:
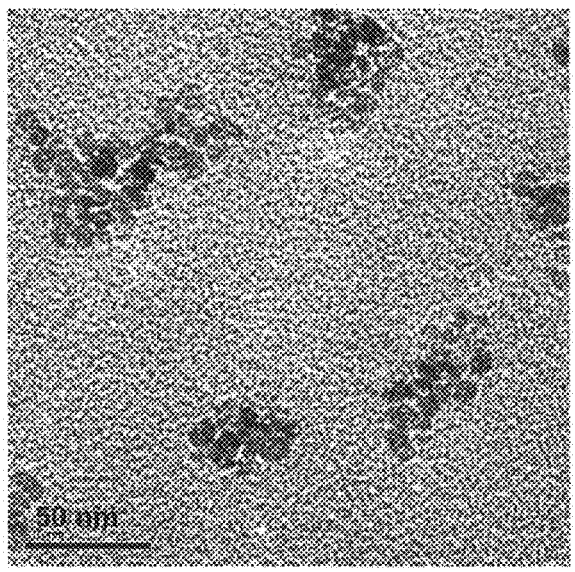
FIG. 4 shows a transmission electron microscopy (TEM) micrograph image of an oleic acid-coated (OA-coated) magnetite NP [Fe(acac)$_3$:NaBH$_4$=1 mmol:40 mmol] IONP-OA$_{40(80)}$. The scale bar is 50 nanometers.

FIG. 4 shows a TEM image of the IONP-OA$_{40(80)}$, showing a particle size of about 12 nanometers.

Figure 8:
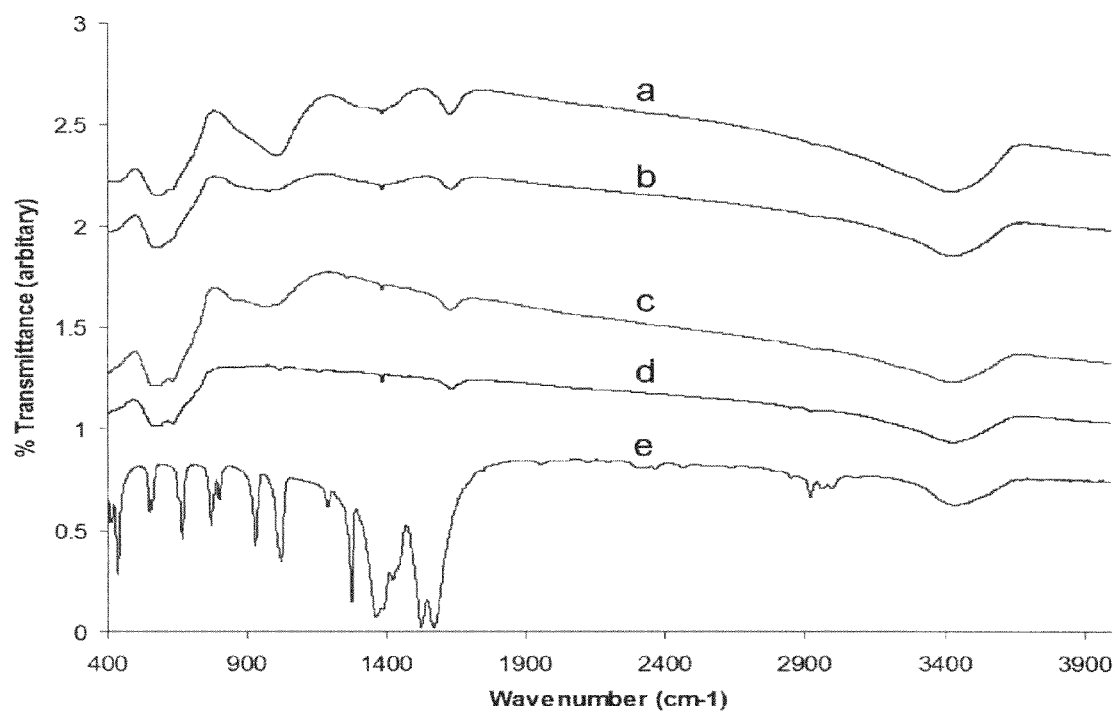
FIG. 8 shows the FT-IR spectra of (a) PEG-coated magnetite NP [Fe(acac)$_3$:NaBH$_4$=1 mmol:40 mmol] IONP-PEG$_{40(80)}$, (b) PEG-coated magnetite NPs IONP-PEG$_{10(80)}$ [Fe(acac)$_3$:NaBH$_4$=1 mmol:10 mmol], (c) bare magnetite NP [Fe(acac)$_3$:NaBH$_4$=1 mmol:40 mmol] IONP$_{40(80)}$, (d) bare magnetite NP [Fe(acac)$_3$:NaBH$_4$=1 mmol:10 mmol] IONP$_{10(80)}$, and (e) Fe(acac)$_3$.

FIG. 8 shows the FT-IR spectra obtained for the series of synthesized IONPs ((a) IONP-PEG$_{40(80)}$, (b) IONP-PEG$_{10(80)}$, (c) IONP$_{40(80)}$, (d) IONP$_{10(80)}$, and (e) Fe(acac)$_3$). Peaks around 580 cm$^{-1}$ and 2900 cm$^{-1}$ correspond to the Fe—O and C—H stretching, respectively. The broad peaks around 3400 cm$^{-1}$ can be assigned to the O—H stretching.

Figure 10A:
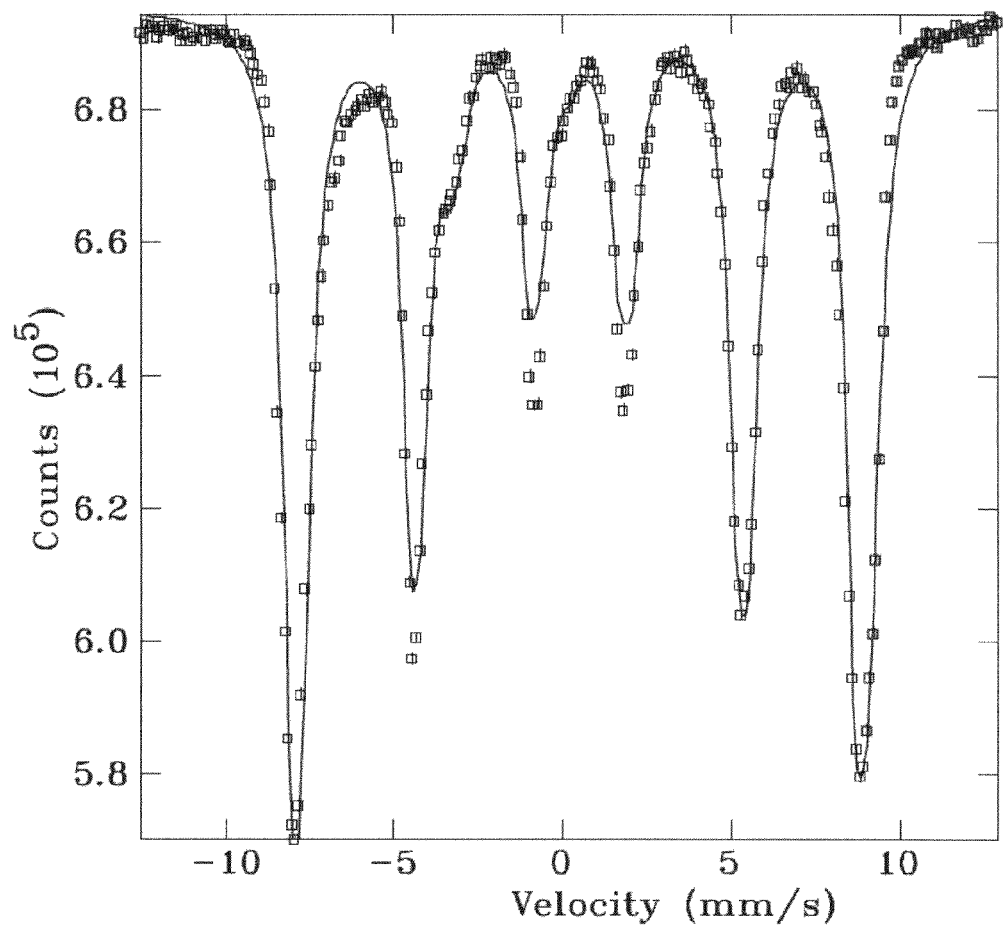
FIGS. 10a and 10b show transmission Mossbauer spectra (a) at 10 K of bare magnetite NP [Fe(acac)$_3$:NaBH$_4$=1 mmol:10 mmol] IONP$_{10(80)}$, and (b) at 5 K of bare magnetite NP [Fe(acac)$_3$:NaBH$_4$=1 mmol:40 mmol] IONP$_{40(80)}$. The solid lines are from a non-linear least squares fit with a model based on two sextets of Lorentzians with independent linewidths.
Figure 10B:
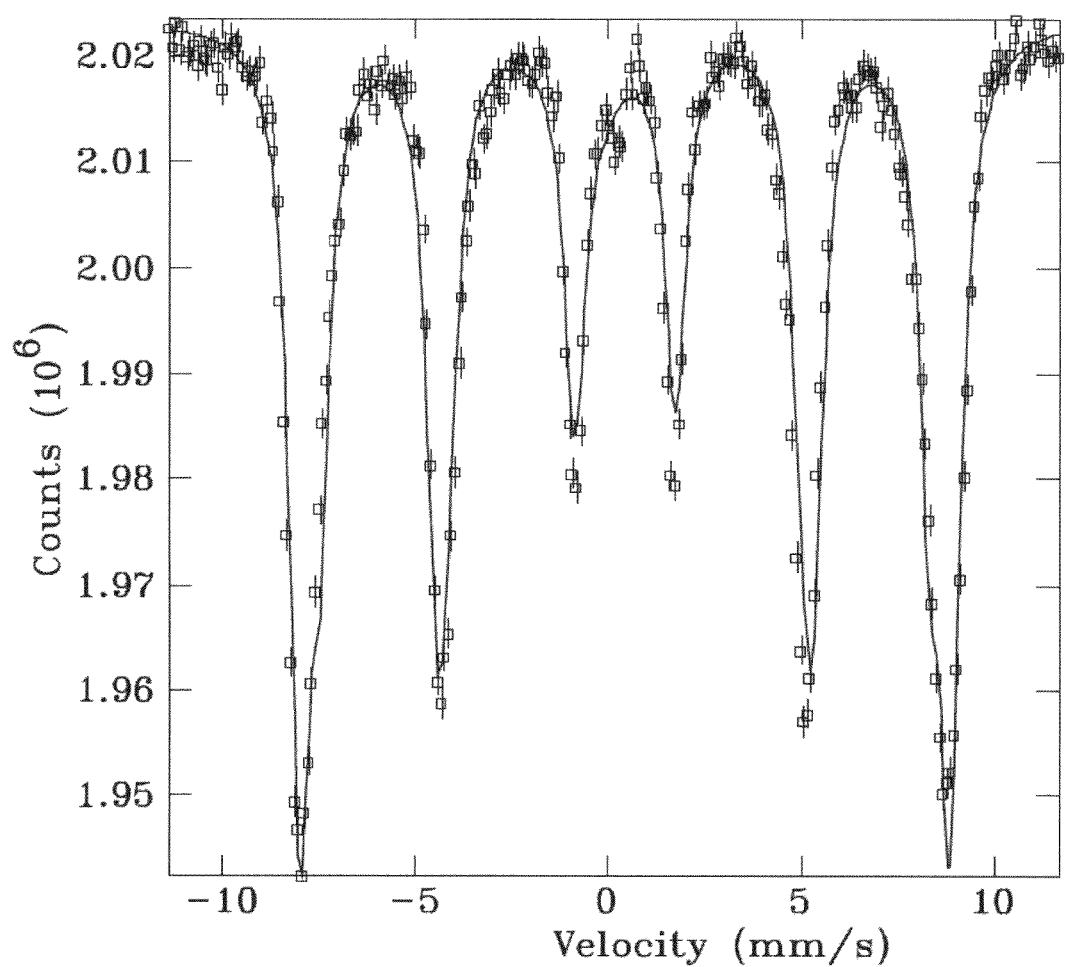

A Mössbauer spectrum of IONP$_{10(80)}$ was collected at 5 K and that of IONP$_{40(80)}$ at 10 K, and both are shown in FIGS. 10a and 10b, respectively. Two sextets were used to describe the iron in octahedral and tetrahedral sites of the magnetite. IONP$_{10(80)}$ were well described by the octahedral site of Fe$_3$O$_4$ having a hyperfine field (B$_{hf}$) of 51.92±0.08 T, a chemical isomer shift (IS) value of 0.32±0.03 mm/s, a quadrupole shift (QS) of 0 and a line width (Γ) of 0.14±0.03 mm/s. The sextet used to fit the tetrahedral site had a B$_{hf}$ value of 52.3±0.07 T, IS of 0.65±0.04, a QS of 0 and a Γ value of 0.24±0.03 mm/s. A third sextet used had a small B$_{hf}$ value of 27.20±0.03 T, a IS value of 0.31±0.04 mm/s, a large QS value of 1.51±0.09 mm/s and a line width of 0.11±0.06 mm/s. Although not wishing to be bound by theory, this may show that there is surface spin on surface of the nanoparticles. In case of IONP$_{40(80)}$, two sextets were used to fit the spectra. The first sextet consistent with magnetite exhibited a hyperfine field (B$_{hf}$) of 52.25±0.09 T, a IS value of 0.43±0.006 mm/s, a quadrupole shift (QS) of 0 and a line width (Γ) of 0.16±0.02 mm/s. The second sextet is consistent with maghemite (γ-Fe$_2$O$_3$) contributed to the 29.4% of the total iron oxide composition. The sextet had a B$_{hf}$ value of 48.97±0.16 T, IS of 0.42±0.01, a QS of 0 and a Γ value of 0.13±0.03 mm/s. A singlet with IS value of −0.26±0.03 contributed to 2.87% of the spectra. The fitted values of B$_{hf}$ and IS for IONP$_{10(80)}$ are in good agreement with that of the bulk Fe$_3$O$_4$ and IONP$_{40(80)}$ has both Fe$_3$O$_4$ and γ-Fe$_2$O$_3$. (Hargrove et al., "Mössbauer measurements of magnetite below the Verwey transition," *Solid State Comm.*, 1970, 8, 303-308.)

The as-synthesized IONP$_{10(80)}$, IONP-PEG$_{10(80)}$, IONP$_{40(80)}$ and IONP-PEG$_{40(80)}$ were washed several times with water and methanol, were collected using a rare earth magnet, and were effectively dried under, for example, nitrogen to yield sooty black powders. The magnetite NPs surface-modified with oleic acid (IONP-OA$_{10(80)}$, size ~11 nm) were easily dispersible in non-polar liquids (e.g., solvents) such as hexane.

The calculated sizes of the bare IONPs prepared in Examples 1 and 2 are provided in Table 2.

TABLE 2

IONPs and the molar ratio between Fe(acac)₃ and NaBH₄.

| Nanoparticles | Surfactant | T (° C.) | NaBH₄/Fe(acac)₃ ratio | Size (nm) |
|---|---|---|---|---|
| $IONP_{10(RT)}$ | — | r.t. | 10 | 5.35 ± 0.71 |
| $IONP_{10(80)}$ | — | 80 | 10 | 8.08 ± 0.93 |
| $IONP_{25(80)}$ | — | 80 | 25 | 6.40 ± 0.96 |

TABLE 2-continued

IONPs and the molar ratio between Fe(acac)₃ and NaBH₄.

| Nanoparticles | Surfactant | T (° C.) | NaBH₄/Fe(acac)₃ ratio | Size (nm) |
|---|---|---|---|---|
| $IONP_{40(80)}$ | — | 80 | 40 | 5.18 ± 1.03 |
| $IONP_{60(80)}$ | — | 80 | 60 | 5.35 ± 0.83 |
| $IONP_{80(80)}$ | — | 80 | 80 | 5.53 ± 0.84 |

Figure 2:
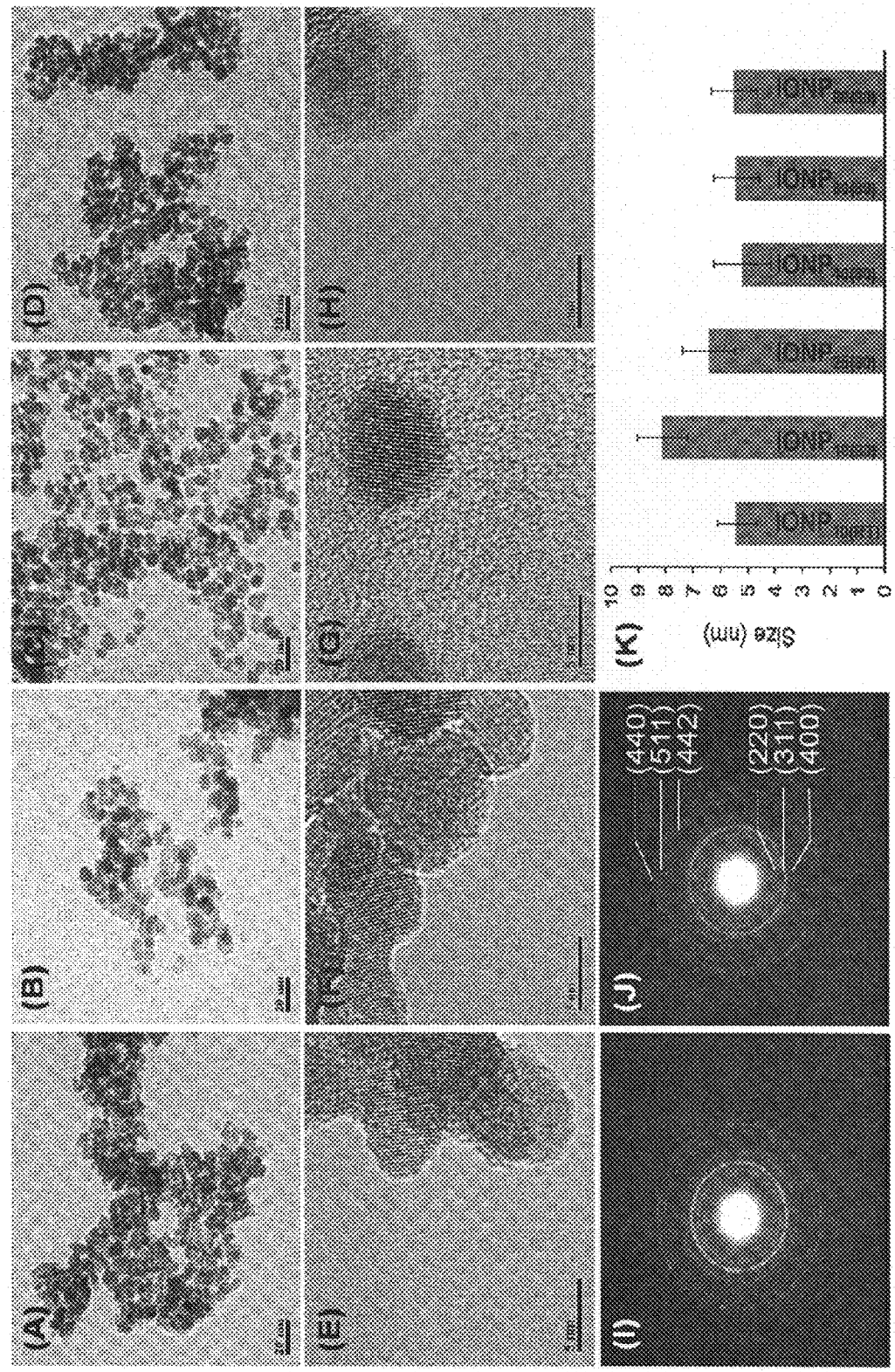
FIG. 2 shows TEM images (scale bar is 20 nanometers) of: (A) IONP$_{10(RT)}$, (B) IONP$_{10(80)}$, (C) IONP$_{25(80)}$, (D) IONP$_{40(80)}$; high resolution TEM (scale bar is 5 nanometers) of (E) IONP$_{10(RT)}$, (F) IONP$_{10(80)}$, (G) IONP$_{25(80)}$, and (H) IONP$_{40(80)}$; selected area electron diffraction (SAED) images: (I) IONP$_{10(RT)}$, (J) IONP$_{10(80)}$, and (K) sizes of the particles represented as the average particle size (mean)±the standard deviation (SD) of at least 200 individual particles for each of the following (from left to right) IONP$_{10(RT)}$, IONP$_{10(80)}$, IONP$_{25(80)}$, IONP$_{40(80)}$, IONP$_{60(80)}$, and IONP$_{80(80)}$.
Figure 3:
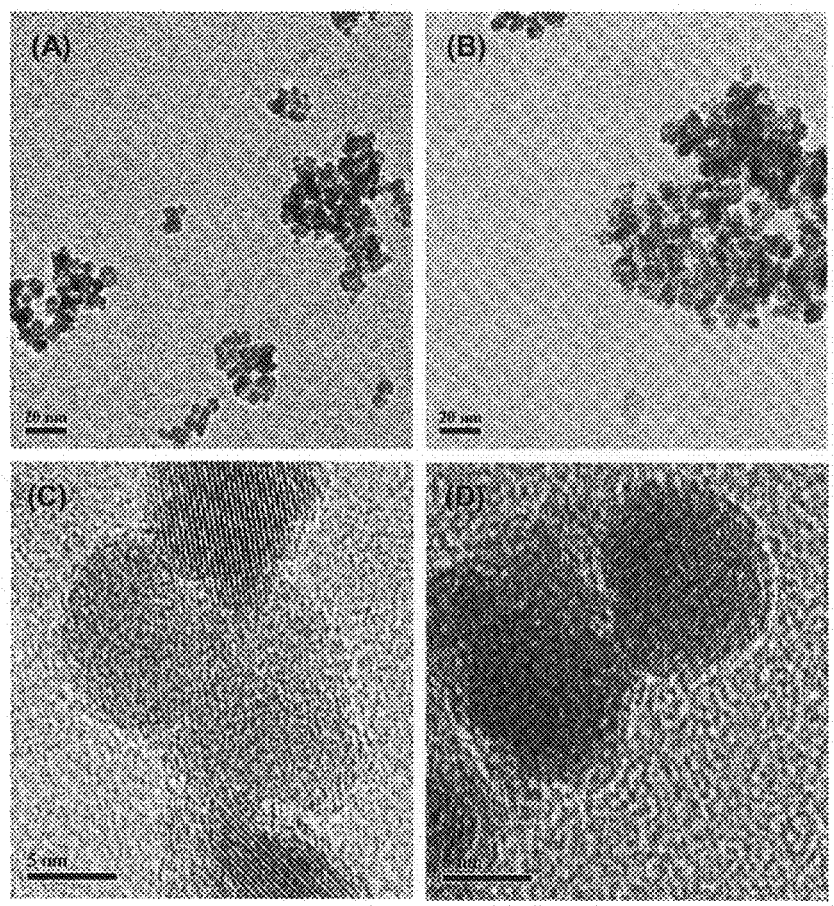
FIG. 3 shows TEM images of: (A) IONP$_{60(80)}$, and (B) IONP$_{60(80)}$; and high-resolution transmission electron microscopy (HRTEM) micrographs of (C) IONP$_{60(80)}$, and (D) IONP$_{60(80)}$.
Figure 6:
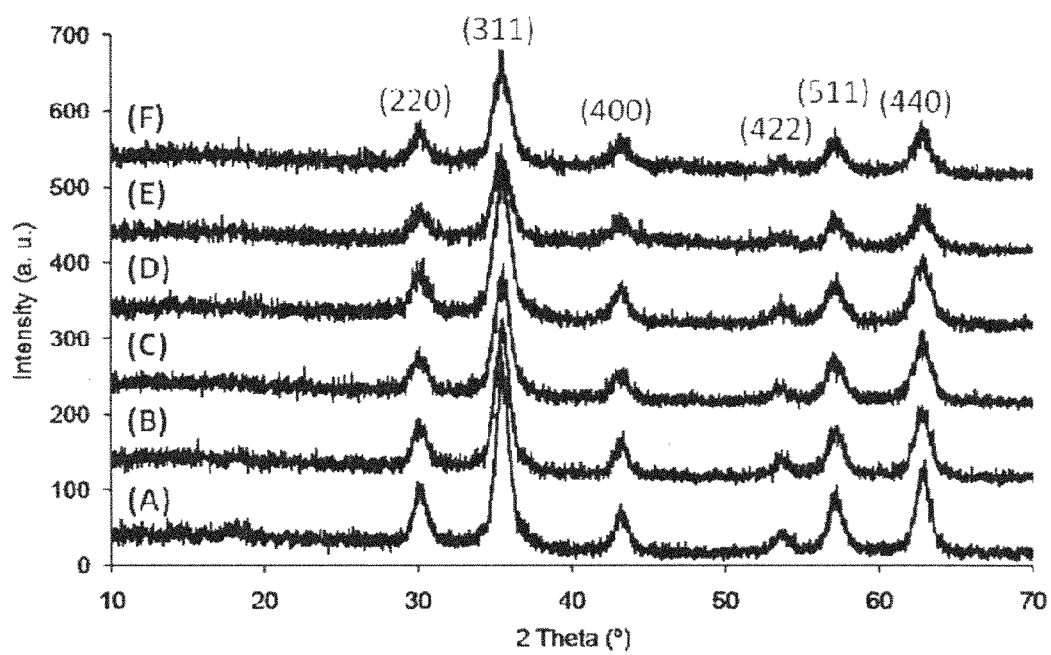
FIG. 6 shows the powder XRD pattern of (A) IONP$_{10(RT)}$, (B) IONP$_{10(80)}$, (C) IONP$_{25(80)}$, (D) IONP$_{40(80)}$, (E) IONP$_{60(80)}$, and (F) IONP$_{80(80)}$.
Figure 7:
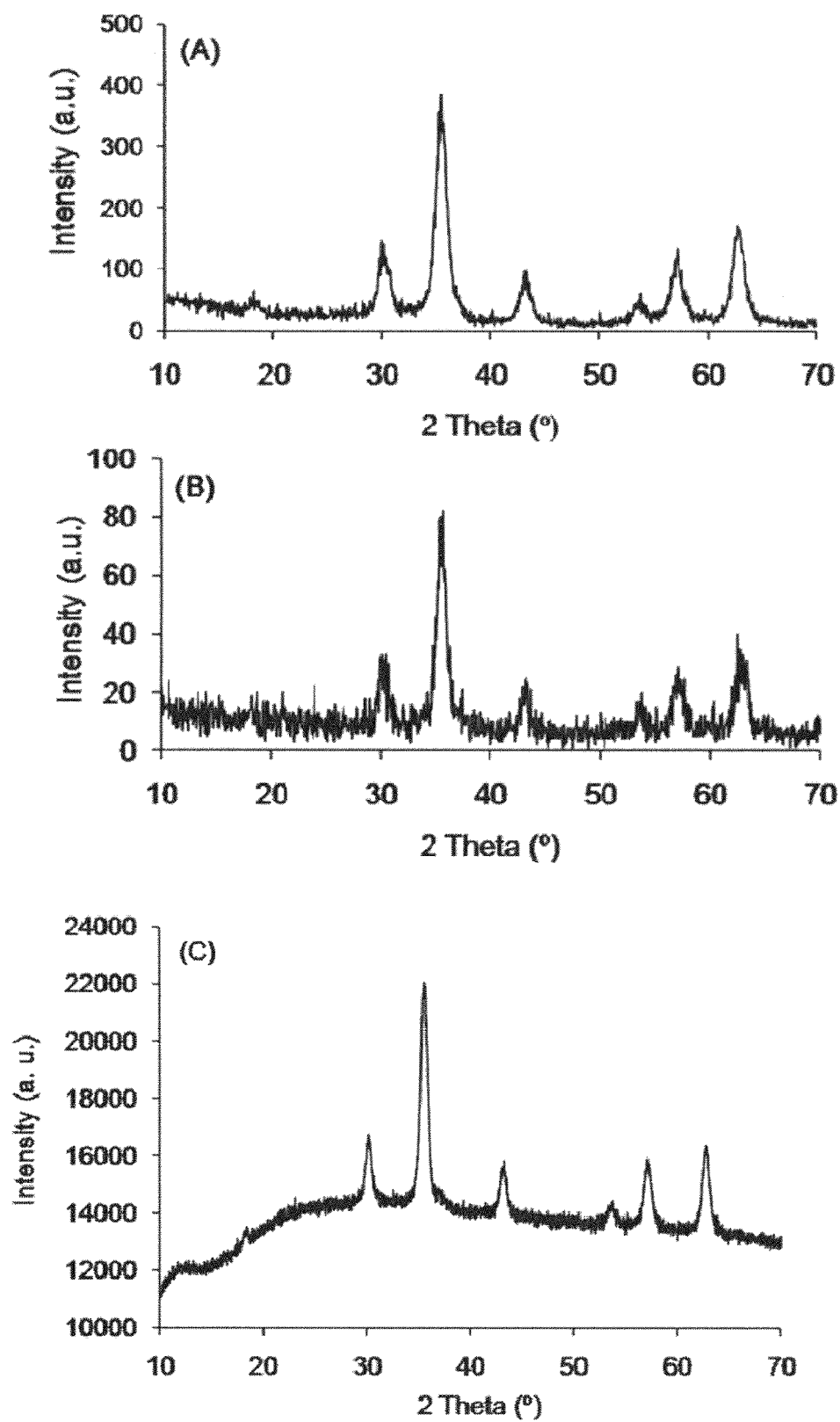
FIG. 7 shows the powder XRD pattern of: (A) IONP-PEG$_{10(RT)}$, IONP-OA$_{10(RT)}$, and (C) glutamic acid-coated (GA-coated) magnetite NP (IONP-GA$_{10(RT)}$).
Figure 11:
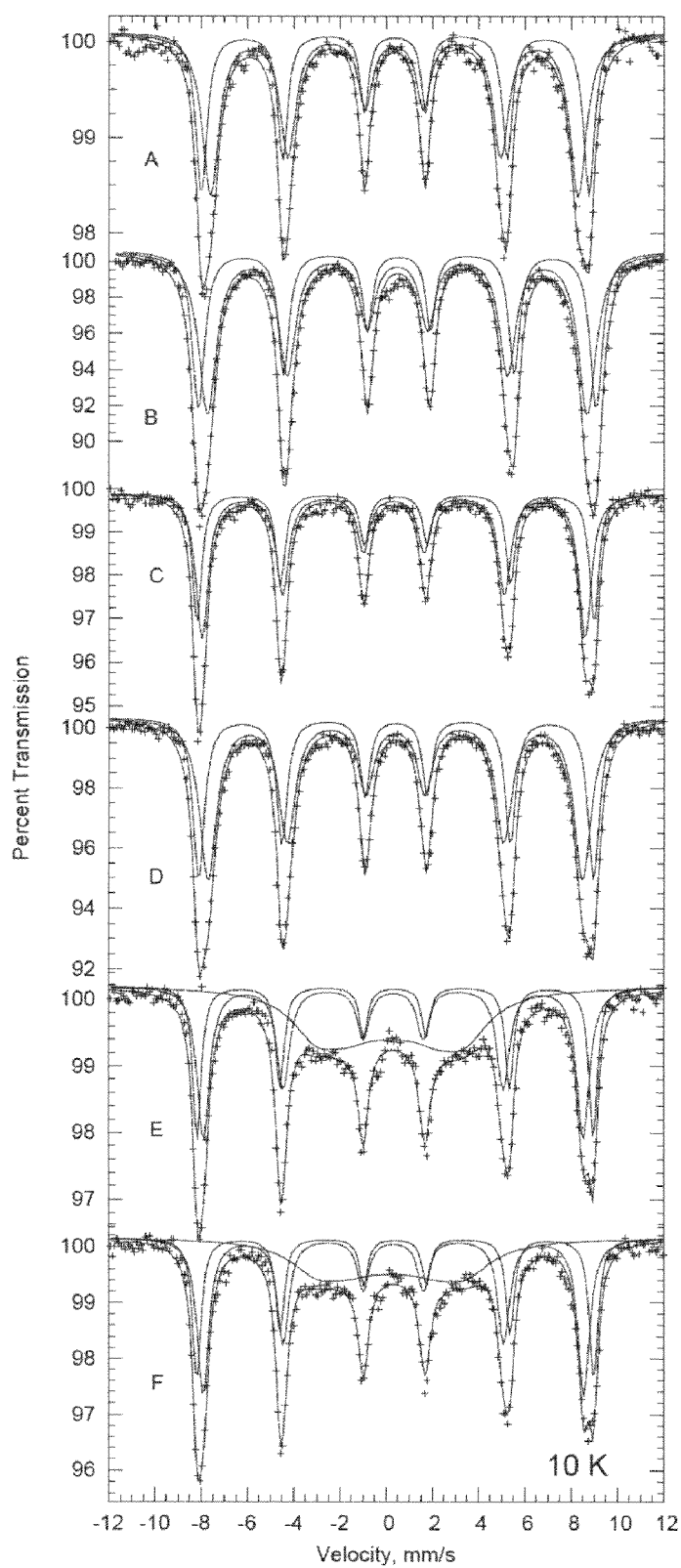
FIG. 11 shows the transmission Mössbauer spectra at 10 K of: (A) IONP$_{10(80)}$, (B) IONP$_{10(80)}$, (C) IONP$_{25(80)}$, (D) IONP$_{40(80)}$, (E) IONP$_{60(80)}$, and (F) IONP$_{80(80)}$. Solid lines are the fits described herein below.

FIG. 6 shows the powder XRD pattern of a series of bare IONPs synthesized at room temperature ($IONP_{10(RT)}$; line (A)) and at 80° C. with sodium borohydride to Fe(acac)₃ molar ratios of 10, 25, 40, 60 and 80 (lines (B), (C), (D), (E), and (F), respectively). From the diffraction pattern and peak positions, $IONP_{10(RT)}$, $IONP_{10(80)}$, $IONP_{25(80)}$ and $IONP_{40(80)}$, $IONP_{60(80)}$ and $IONP_{80(80)}$ were identified as iron oxide with a cubic unit cell, which is consistent with both magnetite and maghemite. The diffraction peaks obtained were broad. Although not wishing to be bound by theory, the broad peaks may have been due to small crystalline domains. The crystalline domain sizes calculated using the Scherrer equation ("Fundamentals of Powder Diffraction and Structural Characterization of Materials," Pecharsky et al. eds., Kluwer Academic Publishers, Boston, Mass., 2003) was approximately 6 nm for $IONP_{10(RT)}$. The average particle sizes of $IONP_{10(RT)}$ from TEM images were determined to be around 5 nm and was in close agreement with the domain sizes from XRD. Lattice fringes were clearly visible in the HRTEM images of the particles in FIGS. 2E-H, which may evidence that the obtained particles may have at least highly crystalline domains, except for $IONP_{60(80)}$ and $IONP_{80(80)}$, where some particles appeared to be poorly crystalline (see FIG. 3 and FIG. 6, lines (E) and (F)). Also the XRD peak intensities for $IONP_{60(80)}$ and $IONP_{80(80)}$ were lower when compared to all other IONPs. The SAED pattern obtained for all particles showed the characteristic ring pattern of magnetite (e.g., FIGS. 2I and 2J, representing $IONP_{10(RT)}$ and $IONP_{10(80)}$, respectively). From the TEM images, the IONPs appeared to be reasonably spherical, which agreed with Lamer's concept of production of monodispersed colloids. (La Mer et al.,"Theory, Production and Mechanism of Formation of Monodispersed Hydrosols," *J. Am. Chem. Soc.*, 1950, 72, 4847-4854.) Transmission Mössbauer spectra were collected at 10 K, well below the superparamagnetic regime. At this temperature, the spectra exhibited a broadened sextet. For the IONPs listed in Table 3, the results of the fits are shown in FIG. 11 and the spectral parameters are given in Table 3.

TABLE 3

Mössbauer spectral parameters obtained from the fit.

| IONPs | H (T) | δ (mm/s²) | $\Delta E_Q$ (mm/s) | Γ (mm/s) | Area (%) (mm/s) | Area (%) |
|---|---|---|---|---|---|---|
| $IONP_{10(RT)}$ | 52(1) | 0.37(1) | 0.008(1) | 0.45(2) | −6.1(1) | 0.4[b] |
|  | 49(1) | 0.34(1) | 0[b] | 0.74(3) | −9.2(1) | 0.6[b] |
| $IONP_{10(80)}$ | 53(1) | 0.50(1) | −0.07(1) | 0.51(2) | −35(1) | 0.4[b] |
|  | 51(1) | 0.47(1) | 0[b] | 0.80(3) | −53(1) | 0.6[b] |
| $IONP_{25(80)}$ | 53(1) | 0.40(1) | 0 | 0.48(1) | −9.1(1) | 0.4[b] |
|  | 51(1) | 0.31(1) | 0[b] | 0.65(2) | −13.2(1) | 0.6[b] |
| $IONP_{40(80)}$ | 53(1) | 0.43(1) | 0.004(9) | 0.50(2) | −20(1) | 0.4[b] |
|  | 51(1) | 0.39(1) | 0 | 0.80(2) | −29(1) | 0.6[b] |
| $IONP_{60(80)}$ | 53(1) | 0.39(1) | 0.16(1) | 0.44(1) | −6.1(1) | 0.24(1) |
|  | 51(1) | 0.31(1) | 0[b] | 0.65(2) | −9.1(1) | 0.36(1) |
|  | 20(3) | 0.23(6) | −0.05(9) | 2.6(2) | −9.9(1) | 0.39(1) |
| $IONP_{80(80)}$ | 53(1) | 0.39(1) | 0.01(1) | 0.45(1) | −7.02(1) | 0.27(1) |
|  | 51(1) | 0.31(1) | 0[b] | 0.61(2) | −10.67(1) | 0.41(1) |
|  | 20(3) | 0.23(7) | −0.1(1) | 2.7(3) | −8.42(1) | 0.32(1) |

[a]The isomer shifts are given relative to room temperature α-iron foil.
[b]Constrained values.

Figure 9:
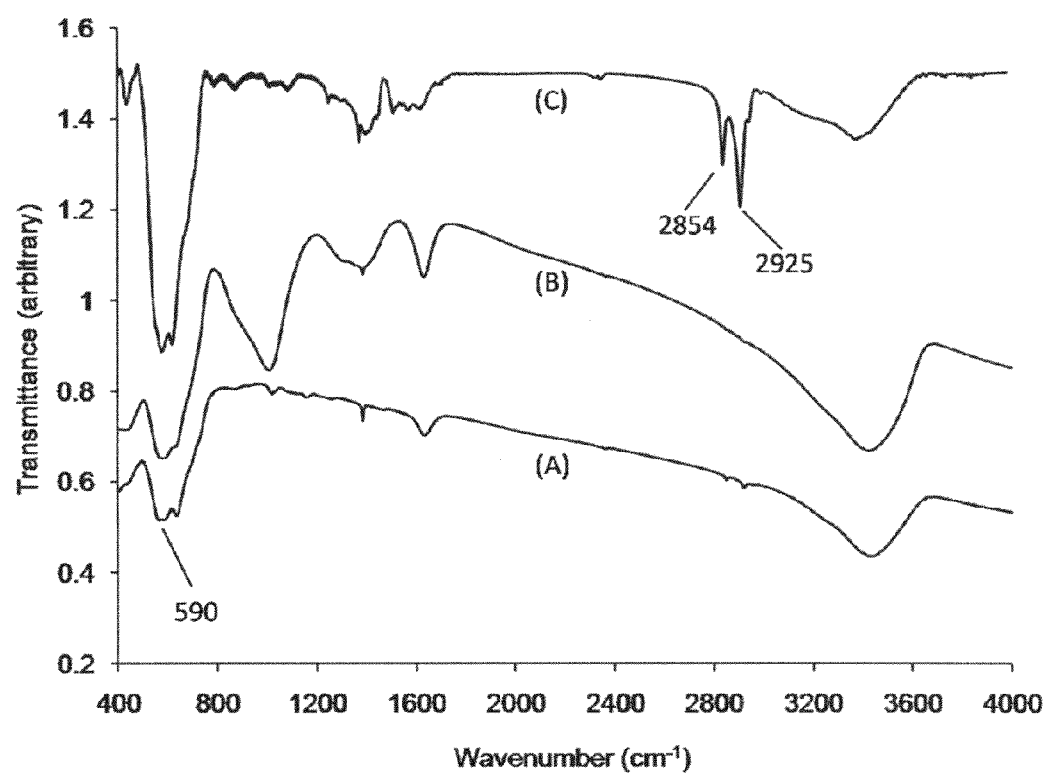
FIG. 9 shows the FT-IR spectra of: (A) IONP$_{10(RT)}$, (B) IONP-PEG$_{10(RT)}$, and (C) IONP-OA$_{10(RT)}$.

The spectra were fitted by two sextets describing the local Fe environments of the octahedral and tetrahedral sites of the IONPs. The quadrupole splitting of the iron octahedral site was constrained to the value of zero. The fitted isomer shifts and hyperfine fields of about 53 T and about 51 T for the tetrahedral and octahedral sites respectively, were in agreement with bulk magnetite ($Fe_3O_4$). (Hargrove et al., "Mössbauer measurements of magnetite below the Verwey transition," *Solid State Commun.*, 1970, 8, 303.) The relative area of each sextet was constrained following the iron crystallographic ratio between the octahedral and tetrahedral site assuming the presence of magnetite. The large fitted linewidths indicated a significant variety of Fe chemical environments in the IONPs and/or a size distribution of NPs. For $IONP_{60(80)}$ and $IONP_{80(80)}$, in addition to the two sextets, the Mössbauer spectra also exhibited an additional highly broadened sextet. It is a simple model that gives a reasonable fit for the spectra. The results of the fits with three components are shown in FIGS. 11E and 11F and the spectral parameters are given in Table 3. The two first sextets were well described by the above hyperfine parameters of magnetite. For the third sextet, the low value of the hyperfine field, about 20 T, and the range of the isomer shifts, about 0.20 mm/s, may assume the presence of a poor crystalline component of iron oxide in these two nanoparticle samples. The PEG-coated IONP-$PEG_{10(80)}$ and OA-coated IONP-$OA_{10(80)}$ were characterized using FT-IR spectroscopy and their transmission spectra are shown in FIG. 9 (lines (B) and (C), respectively). The prominent peaks around 590 cm⁻¹ correspond to the $Fe_{octahedral}$—O—$Fe_{tetrahedral}$ stretching vibrations of spinel iron oxide. The bands at 2854 and 2925 cm⁻¹ for IONP-$OA_{10(80)}$ are related to symmetric and antisymmetric C—H stretching vibrations of the OA coating. The peak for the C—O stretching for polyethylene glycol was indicated by a broad band ranging from 1200 to 1500 cm⁻¹.

Steps involved in the liquid-phase NP synthesis have been an investigated subject. Explanations on the mechanistic pathway of such reactions have been discussed in a number of papers and review articles. (Cushing et al., "Recent Advances in the Liquid-Phase Syntheses of Inorganic Nanoparticles" *Chem. Rev.*, 2004, 104, 3893-3946; Park et al., "Model of Formation of Monodispersed Colloids," *J. Phys. Chem. B*, 2001, 105, 11630-11635; Privman et al., "Mechanism of Formation of Monodispersed Colloids by Aggregation of Nanosize Precursors," *J. Colloid Interface Sci.*, 1999, 213, 36-45.)

The synthesis of IONPs in these examples may follow an aqueous-phase precipitation pathway. The first stage, as in most IONPs syntheses by precipitation, may be nucleation. The IONPs formed initially may be a sparingly soluble species formed under conditions of high concentration (e.g., super-saturation), and the rate of nucleation may be low (e.g., negligible) until a certain concentration (e.g., critical super-saturation) is achieved. Useful super-saturation conditions in this case may be induced by the chemical reduction of $Fe(acac)_3$ by sodium borohydride.

The electrochemical half-reaction of the borohydride ion is shown in Eq(1) and has a standard electrode potential ($E^\circ$) of $-0.481$ V. The borohydride ion may readily reduce the ferric ion in aqueous $Fe(acac)_3$ to a ferrous ion, which has an $E^\circ$ value of 0.77 V as shown in Eq(2). In these examples, the IONPs may be formed directly and the oxygen in the iron oxide NP formed may be supplied by the liquid (e.g., water/ethanol) and/or the acetylacetonate group of the $Fe(acac)_3$. (Niederberger, "Nonaqueous Sol-Gel Routes to Metal Oxide Nanoparticles," *Acc. Chem. Res.*, 2007, 40, 793-800.)

$$B(OH)_3 + 7H^+ + 8e^- \rightleftharpoons BH_4^- + 3H_2O \quad E^\circ = -0.48\text{ V} \quad \text{Eq}(1)$$

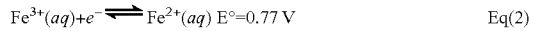

$$Fe^{3+}(aq) + e^- \rightleftharpoons Fe^{2+}(aq) \quad E^\circ = 0.77\text{ V} \quad \text{Eq}(2)$$

$$Fe^{3+} + 3OH^- \rightarrow Fe(OH)_3 \quad \text{Eq}(3)$$

$$Fe(OH)_3 \rightarrow FeOOH + H_2O \quad \text{Eq}(4)$$

$$Fe^{2+} + 2OH^- \rightarrow Fe(OH)_2 \quad \text{Eq}(5)$$

$$2\,FeOOH + Fe(OH)_2 \rightarrow Fe_3O_4 \quad \text{Eq}(6)$$

The IONPs formed in this precipitation pathway may be termed a sparingly soluble species formed under conditions of high supersaturation. The steps involved in the liquid-phase synthesis have, in principle, been studied. (Cushing et al., "Recent Advances in the Liquid-Phase Syntheses of Inorganic Nanoparticles" *Chem. Rev.*, 2004, 104, 3893-3946; Park et al., "Model of Formation of Monodispersed Colloids," *J. Phys. Chem. B*, 2001, 105, 11630-11635; Privman et al., "Mechanism of Formation of Monodispersed Colloids by Aggregation of Nanosize Precursors," *J. Colloid Interface Sci.*, 1999, 213, 36-45.) Although not wishing to be bound by theory, the formation of uniform single crystalline particles may be explained by the La Mer's concept, if the particles formed are very small. LaMer's concept involves two steps, a short nucleation burst followed by diffusional growth of the nuclei to form uniformly sized. particles. (La Mer et al., "Theory, Production and Mechanism of Formation of Monodispersed Hydrosols," *J. Am. Chem. Soc.*, 1950, 72, 4847-4854.) To obtain particles with narrow size distribution, these two steps must be well separated, i.e., nucleation should be avoided during diffusional growth. In the present examples, on addition of sodium borohydride, the pH of the reaction mixture uniformly rose to 11 in every case. This uniform increase in pH may be advantageous in avoiding high local supersaturation, as in the case of addition of base in the co-precipitation method. At higher pH, $Fe(acac)_3$ is hydrolyzed to ferric hydroxide [$Fe(OH)_3$] and ferrous hydroxide [$Fe(OH)_2$] as shown in equation 3 and 5 and, from this stage, the formation of IONPs may follow a precipitation pathway similar to Massart's method. (Privman et al., "Mechanism of Formation of Monodispersed Colloids by Aggregation of Nanosize Precursors," *Colloid Interface Sci.*, 1999, 213, 36-45.) $Fe(OH)_3$ has a much lower solubility, compared to $Fe(OH)_2$, precipitates out first, and is converted into orange-colored goethite, FeOOH (Eq. 4). Nucleation of iron oxide is negligible until a certain critical supersaturation is achieved. The critical supersaturation condition may result from the reaction of goethite with ferrous hydroxide (Eq. 6). At the instance of burst nucleation, large numbers of small nuclei or singlets of iron oxide are formed and their diffusional growth may be governed by the equilibrium critical radius.

After the nucleation, secondary processes such as Ostwald ripening and aggregation may affect the size and morphology of the final product. At the instance of nucleation, large numbers of small particles may be formed, and there may exist an equilibrium NP radius (e.g., equilibrium critical NP radius). Particles with radii greater than the critical radius may continue to grow, while those particles with lower radii may dissolve. (Cushing et al., "Recent Advances in the Liquid-Phase Syntheses of Inorganic Nanoparticles" *Chem. Rev.*, 2004, 104, 3893-3946.) During the growth phase, numerous tiny crystallites may form and may quickly aggregate to form, for example, larger thermodynamically stable NPs. Aggregation during growth phase may be controlled by, for example, a combination of electrostatic and steric repulsion between adjacent particles, caused by chemisorbed charged ions ($OH^-$) and ligands present in the reaction medium. Agglomeration during the growth phase may be controlled by, for example, suitable capping ligands bound to the NPs that may cause steric repulsion between particles. Also, for example, van der Waals repulsions resulting from the chemisorption of charged species (usually $H^+$ or $OH^-$) at the NP surfaces may prevent agglomeration. In the examples having reaction mixtures at 80° C., upon addition of sodium borohydride, the pH of the reaction mixture maintained at 80° C. rose to pH 11. In the case of bare IONP, the van der Waals repulsion from the chemisorbed $Na^+$ ions may provide the control over the size of the final IONP. In Examples 2, 3, 5, and 6, it was observed that the IONPs synthesized using a higher sodium borohydride concentration had a smaller size. Although not wishing to be bound by theory, the reduction in size may be due to the increase in the degree of super-saturation and thereby the number of nucleation sites resulting from the excess sodium borohydride. In Examples 2, 3, 5, and 6, increasing the concentration of sodium borohydride had no effect on the pH; the reaction mixture maintained a pH of 11, and there were more $Na^+$ ions which may chemisorb on NP surfaces and may offer enhanced electrostatic repulsion between growing particles. The resulting smaller size of the IONPs may be a combination of these two effects. Deoxygenating of the liquid prior to the reaction and a nitrogen atmosphere during the reaction may be useful, since the reaction failed to yield IONPs when open to air. Deoxygenating of the liquid and a nitrogen atmosphere during the reaction yielded magnetite of desired purity, and a molar ratio of $NaBH_4$ to $Fe(acac)_3$ of 10:1 and higher appeared to favor burst nucleation. A lower molar ratio of 1:5 $Fe(acac)_3$:$NaBH_4$ did not drive the reaction to completion based on the powder x-ray diffraction (XRD) pattern (see FIG. 5, line e). The ratio of the sodium borohydride to the $Fe(acac)_3$ may be at least one factor in obtaining IONPs of desired purity and size. For example, a molar ratio of 1:10 between $Fe(acac)_3$ and $NaBH_4$ yielded pure magnetite ($IONP_{10(80)}$) as determined by Mossbauer studies. Reaction temperature may also be at least one factor in obtaining IONPs of desired purity and size. $IONP_{10(RT)}$, synthesized at room temperature with a $NaBH_4/Fe(acac)_3$ molar ratio of 10:1 had a size of around 5 nm, as established by transmission electron microscopy (TEM). On increasing the reaction temperature from room temperature (RT) to 80° C. as in the case of $IONP_{10(80)}$, the size of the particles obtained were around 8 nm. IONPs synthesized at 80° C. with an increasing molar ratio of $NaBH_4/Fe(acac)_3$ of 40:1 yielded $IONP_{40(80)}$ with size of around 5 nm. On reducing the molar ratio between borohydride and $Fe(acac)_3$, the average size of the particles increased, as observed by TEM and XRD for $IONP_{25(80)}$ and $IONP_{10(80)}$ in almost a linear fashion (see FIG. 2K). Although not wishing to be bound by theory, the reduction in size with increasing sodium borohydride concentration could be rationalized by an increase in the nucleation burst at a given point in time and a slow down of diffusional growth. The poorly crystalline component resulting from the higher borohydride concentration in $IONP_{60(80)}$ and $IONP_{80(80)}$ may be the result of a kinetically-driven growth phase. Synthesis may be very sensitive to various parameters and variation in reaction conditions may result in a variation in the composition of the final product. With the use of a single iron precursor and fewer reactants, the variables in this reaction are relatively few and are able to make IONPs that are purely magnetite.

Figure 12A:
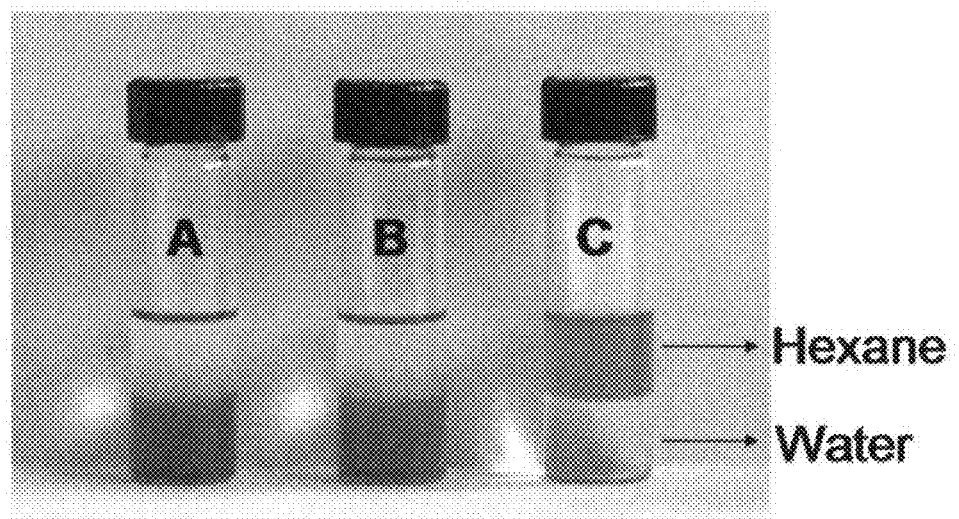
FIG. 12a shows an image of three vials having organic and aqueous fluids: PEG-coated magnetite NPs IONP-PEG$_{10(80)}$ [Fe(acac)$_3$:NaBH$_4$=1 mmol:10 mmol] in the aqueous phase (water) (vial A), bare magnetite NP [Fe(acac)$_3$:NaBH$_4$=1 mmol:10 mmol] IONP$_{10(80)}$ in the aqueous phase (water) (vial B), and oleic acid-coated magnetite NPs (IONP$_{10(80)}$→OA) in the organic phase (hexane) obtained from IONP$_{10(80)}$ by sonication (vial C).
Figure 12B:
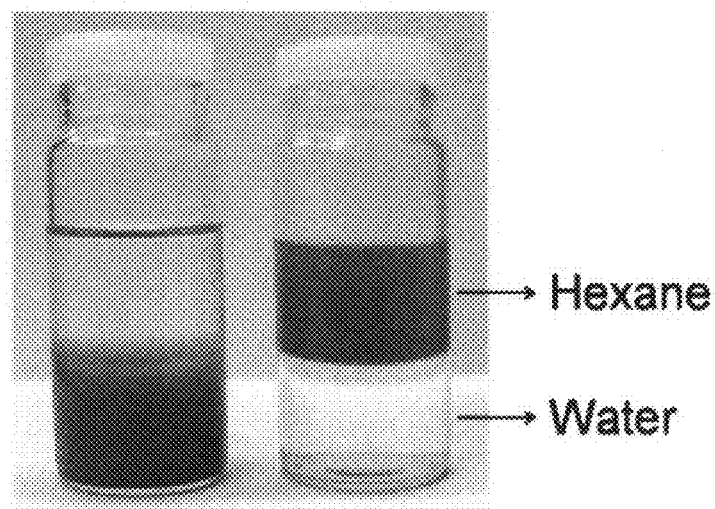
FIG. 12b shows an image of two vials having organic and aqueous fluids: IONP$_{10(RT)}$ in the aqueous phase (water) (left Vial) and oleic acid-coated magnetite NPs (IONP$_{10(RT)}$→OA) in the organic phase (hexane) obtained after sonication of IONP$_{10(RT)}$ and oleic acid (right vial).

The as-synthesized bare IONPs were dispersible in water, physiological buffer, and cell culture media under mild sonication in a sonication bath. FIG. 12a shows the $IONP\text{-}PEG_{10(80)}$ and $IONP_{10(80)}$ dispersed in water (FIG. 12a, vials A and B). In spite of repeated sonication in water/hexane mixtures for 30 minutes, $IONP_{10(80)}$ and $IONP\text{-}PEG_{10(80)}$ did not migrate into the hexane phase. The bare IONPs, apart from in-situ surface modification, can be modified at a later stage with hydrophilic or hydrophobic molecules (FIG. 12b). As an example, bare $IONP_{10(RT)}$ were coated with lipophilic OA post-synthesis in a simple sonication bath. However, $IONP_{10(80)}$ that formed a stable colloid in water, readily migrated and dispersed into the hexane phase in the presence of oleic acid in water/hexane (1:1=v:v) after sonication for 5 min at 30° C. showing that the bare IONPs may also be post-synthesis functionalized with oleic acid. The magnetite NP modified with oleic acid ($IONP_{10(80)}\rightarrow OA$ (FIG. 12a, vial C) formed stable dispersions in hexane that lasted for several months.

FIG. 12b shows the $IONP\text{-}IONP_{10(RT)}$ dispersed in water/hexane (FIG. 12b, left vial). The initially bare nanoparticles in water readily migrated and dispersed into the hexane layer in the presence of OA in water/hexane (1:1=v:v) after 10 minutes of sonication at 25° C. showing the formation of OA-coated $IONP_{10(RT)}\rightarrow OA$ (FIG. 12b, right vial). $IONP_{10(RT)}\rightarrow OA$, like $IONP\text{-}OA_{10(RT)}$, formed stable dispersions in hexane lasting over several months.

Figure 13:
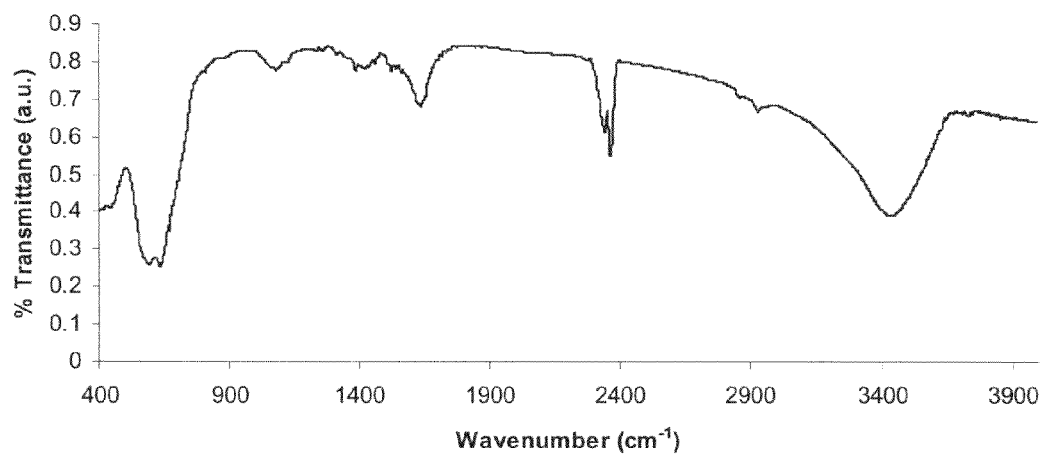
FIG. 13 shows the FT-IR spectra of the glutamic acid-coated magnetite NP [Fe(acac)$_3$:NaBH$_4$=1 mmol:10 mmol] IONP-GA$_{10(80)}$.
Figure 14:
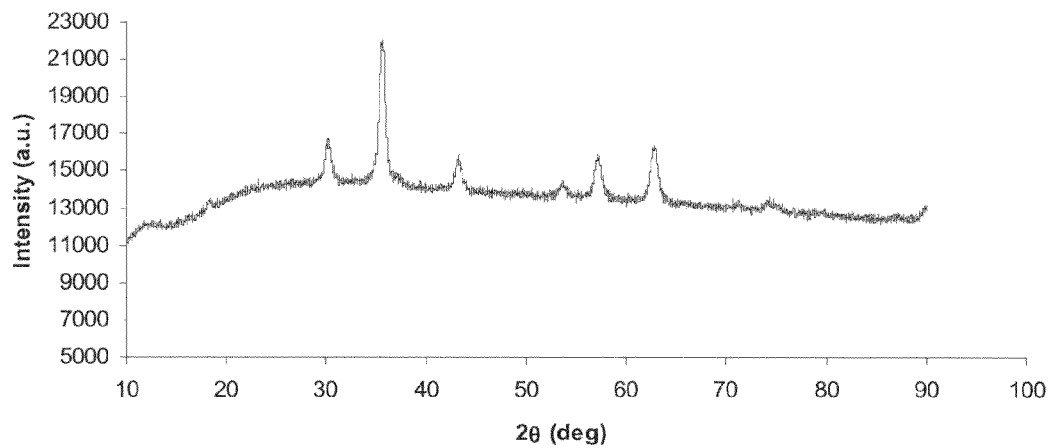
FIG. 14 shows an XRD pattern of the glutamic acid-coated magnetite NP (IONP-GA$_{10(80)}$).

The XRD and FT-IR of $IONP\text{-}GA_{10(80)}$ are shown in FIGS. 13 and 14, respectively.

Figure 15:
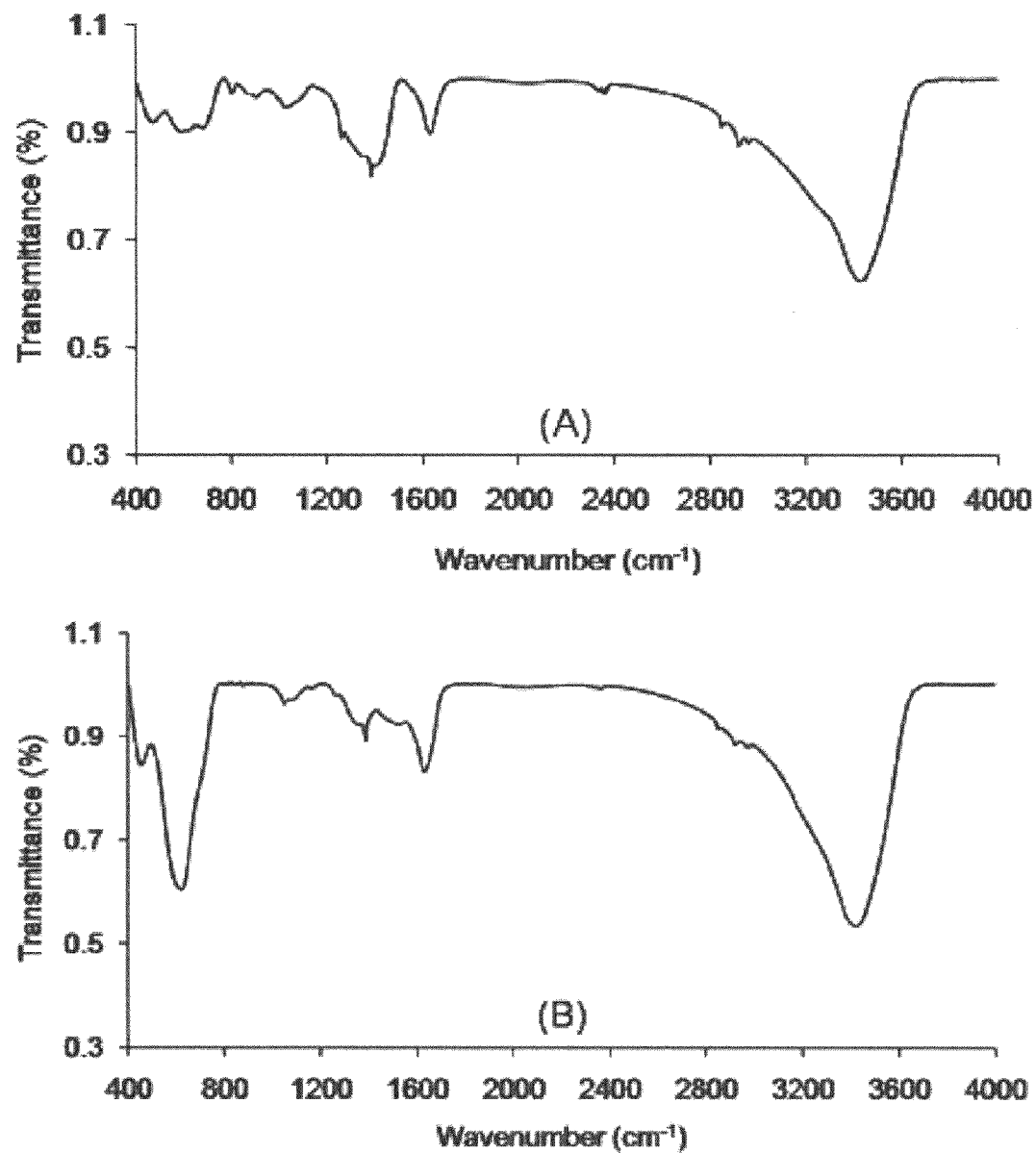
FIG. 15 shows FT-IR spectra of: (A) glutamic acid-coated IONP-GA$_{10(RT)}$ and (B) L-arginine-coated IONP-LA$_{10(RT)}$.

In FIG. 15, FT-IR spectra are shown of (A) L-glutamic acid-coated $IONP\text{-}GA_{10(RT)}$ and (B) L-arginine-coated $IONP\text{-}LA_{10(RT)}$. The strong band from around 2600 $cm^{-1}$ to 3700 $cm^{-1}$ in (A) and (B) encompass O—H stretching of COOH and water of crystallization, N—H stretching of $NH_3^+$ and C—H stretching. The C=O stretching vibrations are revealed as a small peak around 1645 $cm^{-1}$. Fe—O—Fe stretching is evident by peaks around 590 $cm^{-1}$.

Figure 16:
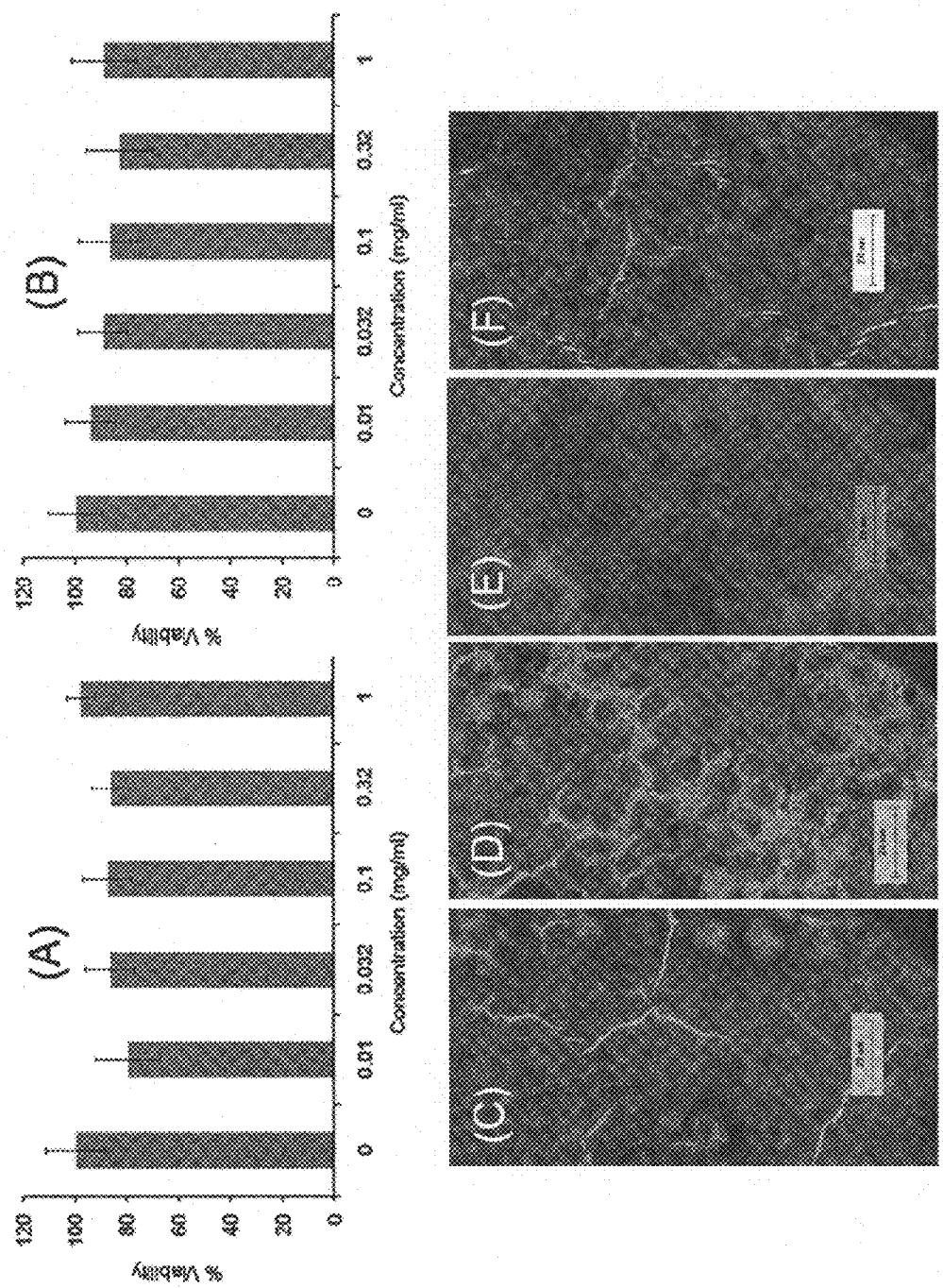
FIG. 16 shows a 3-(4,5-dimethylthiazol-2-yl)-2,5-diphenyltetrazolium bromide (MTT) cytotoxicity assay in: (A) Caco2 and (B) HepG2 cells following 24-hour exposure to various concentrations of IONP$_{10(RT)}$. Values are expressed as percentage of absorbance observed in control wells receiving culture media alone. Each value represents the mean±SD of at least eight wells. Hematoxylin-eosin (HE) staining was carried out to analyze the cell morphology of: (C) control Caco2, (D) Caco2 treated with 1 mg/ml IONP$_{10(RT)}$, (E) control HepG2, and (F) HepG2 treated with 1 mg/ml IONP$_{10(RT)}$. In the images in (C), (D), (E), and (F), the scale bar is 20 micrometers.
Figure 17:
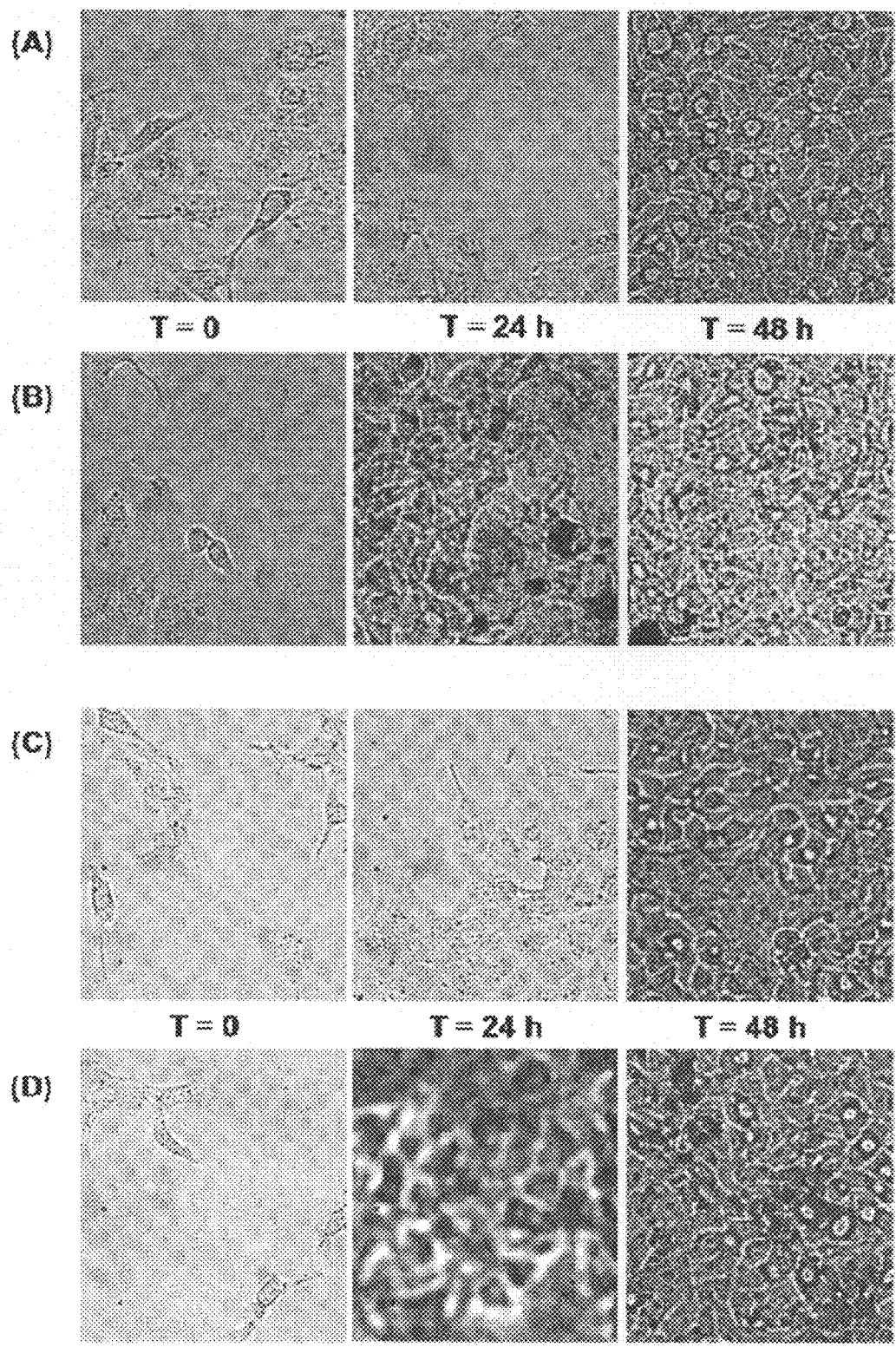
FIG. 17 shows optical microscopy images of: (A) Caco2 cells treated with culture media, (B) Caco2 cells treated with 1 mg/ml of IONP$_{10(RT)}$ in culture media, (C) HepG2 cells treated with culture media, and (D) HepG2 cells treated with IONP$_{10(RT)}$ at different stages prior to MTT assay.

The cell viability or cytotoxicity of the bare $IONP_{10(RT)}$ was investigated in vitro using Caco2 and HepG2 cells as a model system for evaluating intestinal and liver epithelial cell viability, respectively. This testing was conducted to determine if the as-synthesized IONPs were the amount (if any) of toxicity resulting from the synthetic methodology. Cell viability was assessed using the 3-(4,5-dimethylthiazol-2-yl)-2,5-diphenyltetrazolium bromide (MTT) assay, a colorimetric assay based on the cleavage of the yellow MTT salt to purple-coloured formazan by mitochondrial dehydrogenase in viable cells. (Cheng et al., "Characterization of aqueous dispersions of $Fe_3O_4$ nanoparticles and their biomedical applications," *Biomaterials*, 2005, 26, 729-738.) Mitochondria plays a role in maintaining cellular structure and function via aerobic ATP production and may be vulnerable to toxic materials. Both Caco2 and HepG2 cells were not confluent at the time of treatment with the NPs and were confluent prior to the addition of MTT reagent (FIG. 17). From the percentage cell viability (Table 4) of the wells treated with various concentration of $IONP_{10(RT)}$, it can be said that there was no considerable toxicity. Cell morphology was analyzed after 48 hours by fixing the cells on chamber slides followed by hematoxylin-eosin (HE) staining. HE staining is useful in identifying pyknotic or fragmented nuclei resulting from apoptosis or cell death and any irregularities in shape. The nuclei of both Caco2 and HepG2 cells treated with $IONP_{10(RT)}$ were intact, as observed under a phase contrast microscope (FIGS. 16D and 16F), indicating that the cells were viable and morphologically similar to the control cells.

TABLE 4

MTT cell viability assay of Caco2 and HepG2 cells.

| Treatment | Caco2 Cell viability (%) | HepG2 Cell viability (%) |
|---|---|---|
| Control[a] | 99.97 ± 11.27 | 99.97 ± 10.17 |
| 0.010[b] | 79.46 ± 12.54 | 93.97 ± 9.85 |
| 0.032[b] | 86.40 ± 9.36 | 88.88 ± 9.51 |
| 0.100[b] | 87.32 ± 9.23 | 86.45 ± 11.70 |
| 0.320[b] | 85.86 ± 7.18 | 82.40 ± 12.99 |
| 1.000[b] | 97.47 ± 5.48 | 88.60 ± 12.67 |
| 10% EtOH[c] | 11.96 ± 1.45 | 13.50 ± 1.41 |

[a] cell culture media (DMEM).
[b] $IONP_{10(RT)}$ (mg/ml) in DMEM.
[c] 10% ethyl alcohol in DMEM.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A method of making iron-containing nanoparticles, the method comprising:
    contacting an iron-containing precursor with a reducing agent at a temperature less than 200° C. to form a mixture; and
    allowing the mixture to react at a temperature less than 200° C. for a time sufficient to form magnetite nanoparticles, wherein the average size of the magnetite nanoparticles is at least 3 nanometers wherein the iron-containing precursor comprises iron(III) acetylacetonate.

2. The method of claim 1, wherein the reducing agent comprises sodium borohydride.

3. The method of claim 1, wherein the temperature during contacting is greater than 10° C.

4. The method of claim 1, wherein the mixture further comprises a deoxygenated liquid and the contacting occurs in a deoxygenated atmosphere.

5. The method of claim 1, wherein the average size of the magnetite nanoparticles is no greater than 12 nanometers.

6. The method of claim 1, wherein contacting an iron-containing precursor with a reducing agent to form a mixture comprises:
preparing a composition comprising water, an alcohol, and the iron-containing precursor at a temperature of from greater than 10° C. to 85° C.; and
adding a reducing agent to the composition to form the mixture.

7. The method of claim 1, wherein the molar ratio of the iron-containing precursor to the reducing agent is from 1:80 to less than 1:5.

8. The method of claim 1, wherein the method further comprises collecting the magnetite nanoparticles with a magnet, washing the magnetite nanoparticles, and/or drying the magnetite nanoparticles.

9. The method of claim 1, wherein the method further comprises
mixing the magnetite nanoparticles with a hydrophobic surfactant and a non-aqueous liquid to form magnetite nanoparticles that further comprise hydrophobic ligands.

10. The method of claim 9, wherein mixing the magnetite nanoparticles with a hydrophobic surfactant and a non-aqueous liquid comprises sonicating the magnetite nanoparticles with a hydrophobic surfactant and a non-aqueous liquid.

11. The method of claim 1, wherein the nanoparticle formation occurs in the absence of toxic organic surfactants.

12. The method of claim 1, wherein the time sufficient to form magnetite nanoparticles is 30 minutes or less.

13. The method of claim 1, wherein the magnetite nanoparticles are present in an amount of 50 weight percent (wt-%) or more relative to the total weight of nanoparticles formed.

14. A method of making selectively-sized iron-containing nanoparticles, the method comprising:
providing a composition comprising an iron-containing precursor;
adding a reducing agent to the composition to form selectively-sized magnetite nanoparticles, wherein the molar ratio of the iron-containing precursor to the reducing agent is from 1:80 to less than 1:5, wherein the reducing agent comprises sodium borohydride, and allowing the mixture to react at a temperature from greater than 10° C. to 90° C. for a time sufficient to form magnetite nanoparticles.

15. A method of making magnetite nanoparticles, the method comprising:
combining iron(III) acetylacetonate and deoxygenated ethanol with deoxygenated water to form a composition under a nitrogen atmosphere;
adding sodium borohydride to the composition at a temperature from greater than 10° C. to 90° C. to form a mixture;
allowing the mixture to react at a temperature from greater than 10° C. to 90° C. for a time sufficient to form magnetite nanoparticles.

16. The method of claim 15, wherein the composition further comprises a surfactant, wherein the surfactant is not reduced under conditions of magnetite nanoparticle formation.

17. The method of claim 15, wherein the composition further comprises a capping agent, wherein the capping agent is not reduced under conditions of magnetite nanoparticle formation.

18. The method of claim 17, wherein the capping agent is selected from the group consisting of poly(ethylene glycol), oleic acid, L-glutamic acid, R-glutamic acid, L-arginine, and R-arginine.

19. A method comprising using the iron-containing nanoparticles made by the method of claim 1 as a magnetic resonance imaging contrast agent, in magnetically directed drug delivery, in a magnetic recording device, in tumour treatment by hyperthermia, or magnetic tagging of a cell, a virus, a protein, and/or a gene.

* * * * *